(12) United States Patent
Soltani et al.

(10) Patent No.: US 7,648,478 B2
(45) Date of Patent: *Jan. 19, 2010

(54) TREATMENT OF VASCULAR OCCLUSIONS USING ULTRASONIC ENERGY AND MICROBUBBLES

(75) Inventors: Azita Soltani, Snohomish, WA (US); Douglas R. Hansmann, Bainbridge Island, WA (US)

(73) Assignee: Ekos Corporation, Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/046,375

(22) Filed: Mar. 11, 2008

(65) Prior Publication Data

US 2008/0208109 A1 Aug. 28, 2008

Related U.S. Application Data

(63) Continuation of application No. 11/046,208, filed on Jan. 28, 2005, now Pat. No. 7,341,569.

(60) Provisional application No. 60/540,491, filed on Jan. 30, 2004.

(51) Int. Cl.
*A61B 17/20* (2006.01)

(52) U.S. Cl. ..................................... 604/22

(58) Field of Classification Search ............ 604/20–22, 604/96.01, 49, 101.01, 101.02, 101.03, 101.05; 600/437, 466, 462, 467, 469, 470; 606/27–28; 607/96, 97
See application file for complete search history.

(56) References Cited

U.S. PATENT DOCUMENTS

| | | | |
|---|---|---|---|
| 2,961,382 A | 11/1960 | Singher et al. |
| 4,466,442 A | 8/1984 | Hilmann et al. |
| 4,657,543 A | 4/1987 | Langer et al. |
| 4,657,756 A | 4/1987 | Rasor et al. |
| 4,762,915 A | 8/1988 | Kung et al. |
| 4,772,594 A | 9/1988 | Hashimoto et al. |
| 4,774,958 A | 10/1988 | Feinstein |
| 4,797,285 A | 1/1989 | Barenholz et al. |

(Continued)

FOREIGN PATENT DOCUMENTS

EP 1 252 885 A2 10/2002

(Continued)

OTHER PUBLICATIONS

PCT Search Report, PCT Application PCT/US2006/13531; Apr. 12, 2006.
B.D. Butler, Production of Microbubbles for Use as Echo Contrast Agents, J. clin. Ultrasound 14(5): 408-12 (Jun. 1986).
Bao et al., Transfection of a Reporter plasmid into Cultured Cells By Sonoporation In Vitro., Ultrasound in Med. & Biol., vol. 23, Nov. 6, 1997.
Bleeker et al., On the Application of Ultrasonic Contrast Agents for Blood Flowmetry and Assessment of Cardiac Perfusion, J. Ultrasound, Med. 9(8): 461-71 (Aug. 1990).
Feinstein et al., Two-dimensional Contrast Echocardiography I. In Vitro Development and Quantitative Analysis of Echo Contrast Agents, J. Am. Coll. Cardiol. 3(1): 14-20 (Jan. 1984).

(Continued)

*Primary Examiner*—Manuel A Mendez
(74) *Attorney, Agent, or Firm*—Knobbe Martens Olson & Bear, LLP

(57) ABSTRACT

In one embodiment of the present invention, a method of treating a vascular occlusion located at a treatment site within a patient's vasculature comprises positioning an ultrasound catheter at the treatment site. The method further comprises delivering a microbubble therapeutic compound from the ultrasound catheter to the vascular occlusion during a first treatment phase. The method further comprises pausing the delivery of the microbubble therapeutic compound and delivering ultrasonic energy from the ultrasound catheter to the vascular occlusion during a second treatment phase while the delivery of microbubble therapeutic compound remains paused.

25 Claims, 19 Drawing Sheets

U.S. PATENT DOCUMENTS

| | | | |
|---|---|---|---|
| 4,821,740 A | 4/1989 | Tachibana et al. | |
| 4,844,882 A | 7/1989 | Widder et al. | |
| 4,900,540 A | 2/1990 | Ryan et al. | |
| 4,920,954 A | 5/1990 | Alliger et al. | |
| 4,921,478 A | 5/1990 | Solano et al. | |
| 4,936,281 A | 6/1990 | Stasz | |
| 4,948,587 A | 8/1990 | Kost et al. | |
| 4,953,565 A | 9/1990 | Tachibana et al. | |
| 5,007,438 A | 4/1991 | Tachibana et al. | |
| 5,040,537 A | 8/1991 | Katakura | |
| 5,069,664 A | 12/1991 | Guess et al. | |
| 5,088,499 A | 2/1992 | Unger | |
| 5,129,883 A | 7/1992 | Black | |
| 5,149,319 A | 9/1992 | Unger | |
| 5,156,050 A | 10/1992 | Schmid et al. | |
| 5,158,071 A | 10/1992 | Umemura et al. | |
| 5,197,946 A | 3/1993 | Tachibana | |
| 5,261,291 A | 11/1993 | Schoch et al. | |
| 5,269,291 A | 12/1993 | Carter | |
| 5,277,913 A | 1/1994 | Thompson et al. | |
| 5,315,998 A | 5/1994 | Tachibana et al. | |
| 5,318,014 A | 6/1994 | Carter | |
| 5,342,292 A | 8/1994 | Nita et al. | |
| 5,342,608 A | 8/1994 | Moriya et al. | |
| 5,362,309 A | 11/1994 | Carter | |
| 5,368,036 A | 11/1994 | Tanaka et al. | |
| 5,380,273 A | 1/1995 | Dubrul et al. | |
| 5,431,663 A | 7/1995 | Carter | |
| 5,440,914 A | 8/1995 | Tachibana et al. | |
| 5,474,531 A | 12/1995 | Carter | |
| 5,542,935 A | 8/1996 | Unger et al. | |
| 5,558,092 A | 9/1996 | Unger et al. | |
| 5,580,575 A | 12/1996 | Unger et al. | |
| 5,585,112 A | 12/1996 | Unger et al. | |
| 5,628,728 A | 5/1997 | Tachibana et al. | |
| 5,630,837 A | 5/1997 | Crowley | |
| 5,648,098 A | 7/1997 | Porter | |
| 5,695,460 A | 12/1997 | Siegel et al. | |
| 5,707,608 A | 1/1998 | Liu | |
| 5,713,848 A | 2/1998 | Dubrul et al. | |
| 5,718,921 A | 2/1998 | Mathiowitz et al. | |
| 5,733,572 A | 3/1998 | Unger et al. | |
| 5,735,811 A | 4/1998 | Brisken | |
| 5,776,429 A | 7/1998 | Unger et al. | |
| 5,817,048 A | 10/1998 | Lawandy | |
| 5,836,896 A | 11/1998 | Rosenschein | |
| 5,916,192 A | 6/1999 | Nita et al. | |
| 5,997,497 A | 12/1999 | Nita et al. | |
| 6,001,069 A | 12/1999 | Tachibana et al. | |
| 6,024,718 A | 2/2000 | Chen et al. | |
| 6,068,857 A | 5/2000 | Weitschies et al. | |
| 6,096,000 A | 8/2000 | Tachibana et al. | |
| 6,096,070 A | 8/2000 | Ragheb et al. | |
| 6,113,558 A | 9/2000 | Rosenschein et al. | |
| 6,135,976 A | 10/2000 | Tachibana et al. | |
| 6,176,842 B1 | 1/2001 | Tachibana et al. | |
| 6,210,356 B1 | 4/2001 | Anderson et al. | |
| 6,228,046 B1 | 5/2001 | Brisken | |
| 6,287,271 B1 | 9/2001 | Dubrul et al. | |
| 6,296,619 B1 | 10/2001 | Brisken et al. | |
| 6,416,740 B1 | 7/2002 | Unger | |
| 6,508,816 B2 | 1/2003 | Shadduck | |
| 6,524,251 B2 | 2/2003 | Rabiner et al. | |
| 6,548,047 B1 | 4/2003 | Unger | |
| 6,582,392 B1 | 6/2003 | Bennett et al. | |
| 6,723,063 B1 | 4/2004 | Zhang et al. | |
| 6,896,659 B2 | 5/2005 | Conston et al. | |
| 7,220,239 B2 | 5/2007 | Wilson et al. | |
| 7,341,569 B2 * | 3/2008 | Soltani et al. ................. 604/22 | |
| 7,384,407 B2 | 6/2008 | Rodriguez et al. | |
| 2001/0003790 A1 | 6/2001 | Ben-Haim et al. | |
| 2001/0053384 A1 | 12/2001 | Greenleaf et al. | |
| 2002/0041898 A1 | 4/2002 | Unger et al. | |
| 2003/0139774 A1 | 7/2003 | Epstein et al. | |
| 2004/0019318 A1 | 1/2004 | Wilson et al. | |
| 2004/0068189 A1 | 4/2004 | Wilson et al. | |
| 2006/0264809 A1 | 11/2006 | Hansmann et al. | |
| 2007/0083120 A1 | 4/2007 | Cain et al. | |

FOREIGN PATENT DOCUMENTS

| | | |
|---|---|---|
| JP | 2 180275 A | 7/1990 |
| WO | WO 80/01365 A1 | 7/1980 |
| WO | WO 89/05159 A1 | 6/1989 |
| WO | WO 89/05160 A1 | 6/1989 |
| WO | WO 95/15118 A1 | 6/1995 |
| WO | WO 96/15815 A1 | 5/1996 |
| WO | WO 99/39738 A1 | 8/1999 |

OTHER PUBLICATIONS

Greenleaf et al., Artificial Cavitation Nuclei Significantly Enhance Acoustically Induced Cell Transfection, Ultrasound in Med. & Biol., vol. 24, No. 4 pp. 587-595, 1998.

Holland and R.E. Apfel, Thresholds for Transient Cavitation Produced by Pulsed Ultrasound in a Controlled Nuclei Environment, J. Acoust. Soc. Am. 88(5): 2059-2069 (Nov. 1990).

Jeffers et al., Evaluation of the Effect of Cavitation Activity on Drug-Ultrasound Synergisms, Ultrasonics Symposium 1993.

Jeffers et al., Dimethylformamide as an Enhancer of Cavitation-Induced Cell Lysis In Vitro, J. Acoust. Soc. Am. vol. 97, No. 1, Jan. 1995.

Keller et al., Automated Production and Analysis of Echo Contrast Agents, J. Ultrasound Med. 5(9): 493-8 (Sep. 1986).

Kim, T.F., Microbubbles Show Promise for Enhancing Ultrasound Signal, Image, Other Applications, Medical news & Perspectives, JAMA 261(11): 1542 (Mar. 17, 1989).

Lang et al., Contrast Ultrasonography of the Kidney: a New Method for Evaluation of Renal Perfusion in Vivo, Circulation 75(1): 229-234 (Jan. 1987).

Leong et al., Polyanhydrides for Controlled Release of Bioactive Agents, Biomaterials, vol. 7: 364-371 (Sep. 1986).

Meltzer et al., The Source of Ultrasound Contrast Effect, J. Clin. Ultrasound 8(2): 121-7 (Apr. 1980).

Miller et al., Sonoporation of Cultured Cells in the Rotation Tube Exposure System, Ultrasound in Med. & Biol., vol. 25, No. 1, 1999.

Porter et al., Thrombolytic Enhancement With Perfluorocarbon-Exposed Sonicated Dextrose Albumin Microbubbles, American Heart Journal, Nov. 1996.

Prat et al., In Vivo Effects of Cavitation Alone or in Combination Wity Chemotherapy in a Peritoneal Carcinomatosis in the Rat, British Journal or Cancer vol. 68, pp. 13-17.

Price et al., Delivery of Colloidal Particles and Red Blood Cells to Tissue Through Microvessel Ruptures Created By Targeted Microbubble Destruction With Ultrasound, Circulation 19:1264-1267, Sep. 29, 1998.

Tachibana K., Tachibana s., Albumin Microbubble Echo-Contrast Materials as an Enhancer For Ultrasound Accelerated Thrombolysis, Circulation, 92:1148-1150, Sep. 1, 1995.

Unger et al., Ultrasound Enhances Gene Expression of Liposomal Transfection. vol. 32, No. 12, Dec. 1997.

Unger et al., Acoustically Active Liposheres Containing Paclitaxel, vol. 11, No. 12, 1992.

Vandenburg et al., Myocardial Risk Area and Peak Gray Level Measurement by Contrast Echocardiography: Effect of Microbubble Size and Concentration, Injection Rate, and Coronary Vasodilation, Am. Heart J., 115(4), 733-9 (Apr. 1988).

Wheatly et al., Contrast Agents for Diagnostic Ultrasound: Development and Evaluation of Polymer-Coated Microbubbles, Biomaterials 11(19): 713-7 (Nov. 1990).

Wu et al., Binding as Lysing of Blood Clots Using MRX-408, Investigative Radiology, vol. 33, No. 12, May 1998.

* cited by examiner

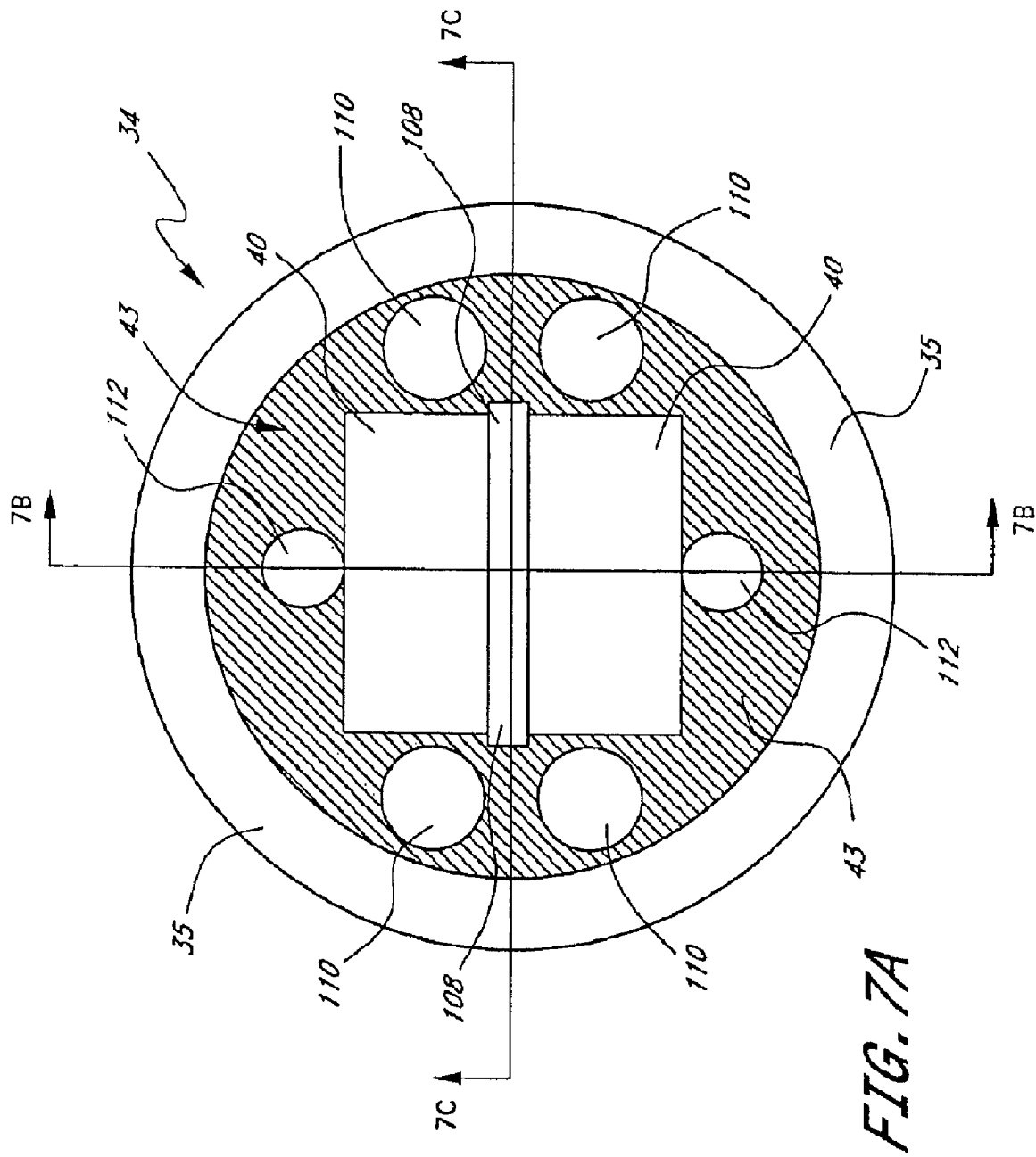

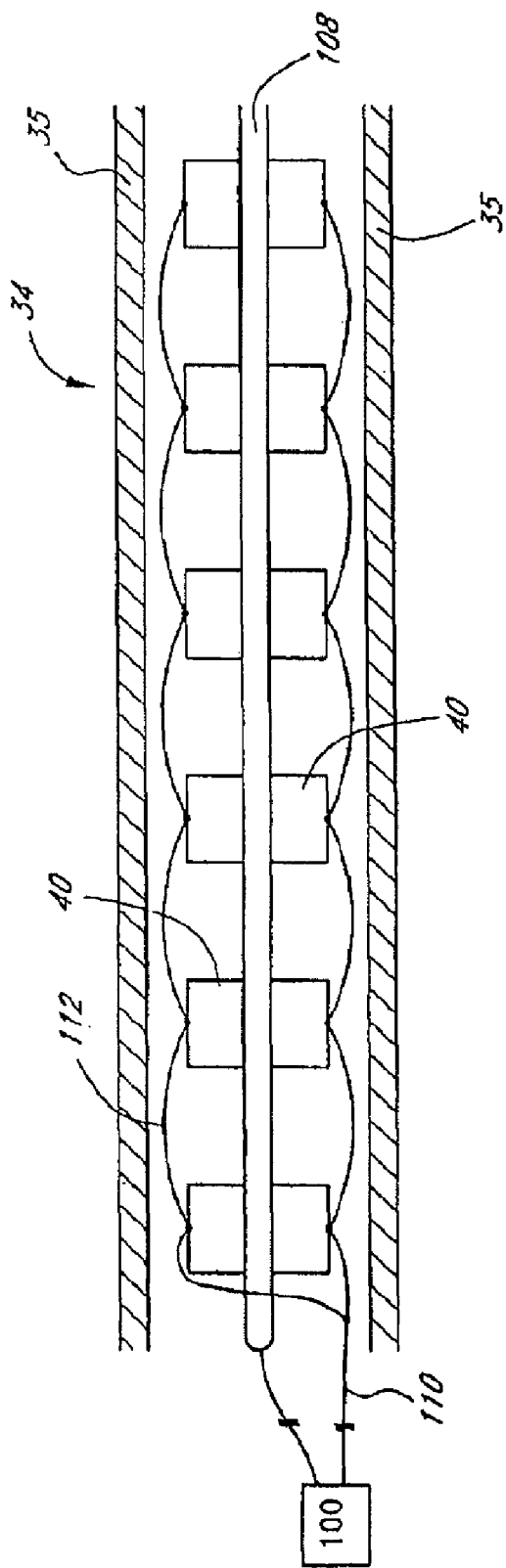
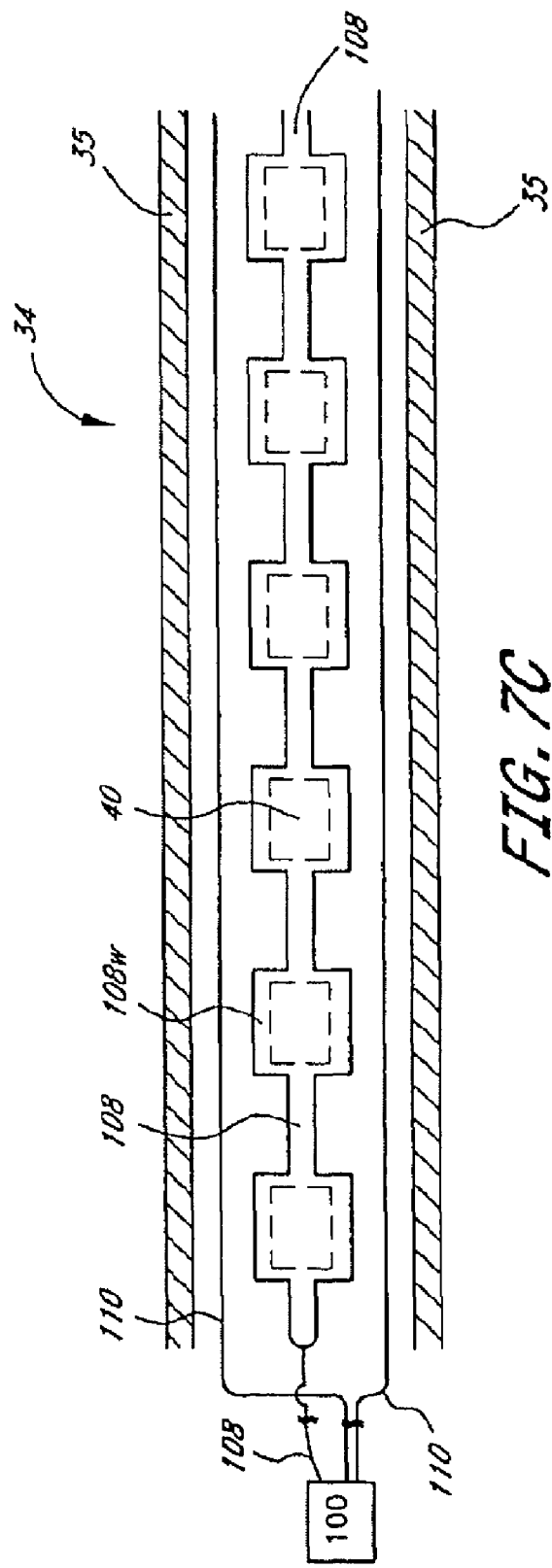

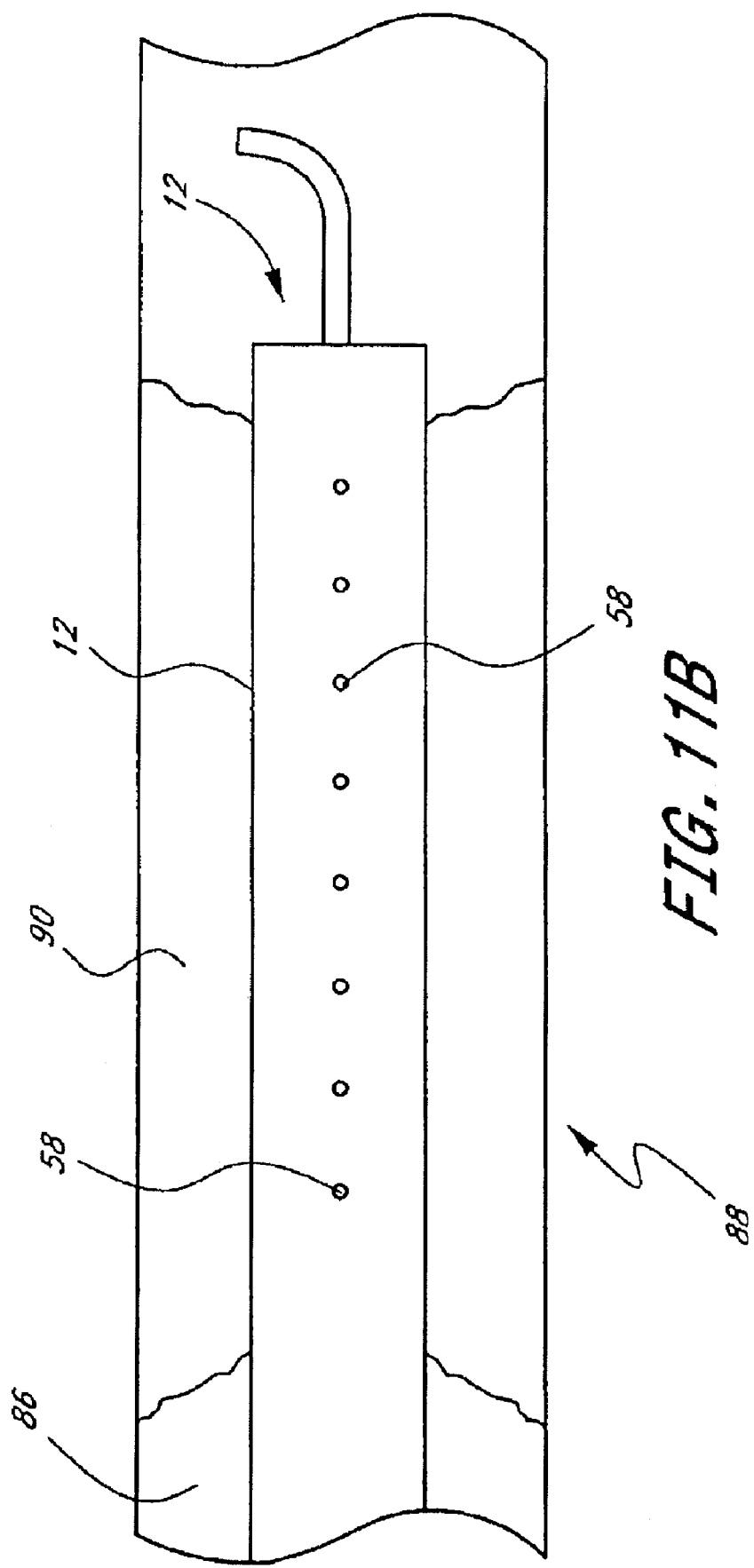

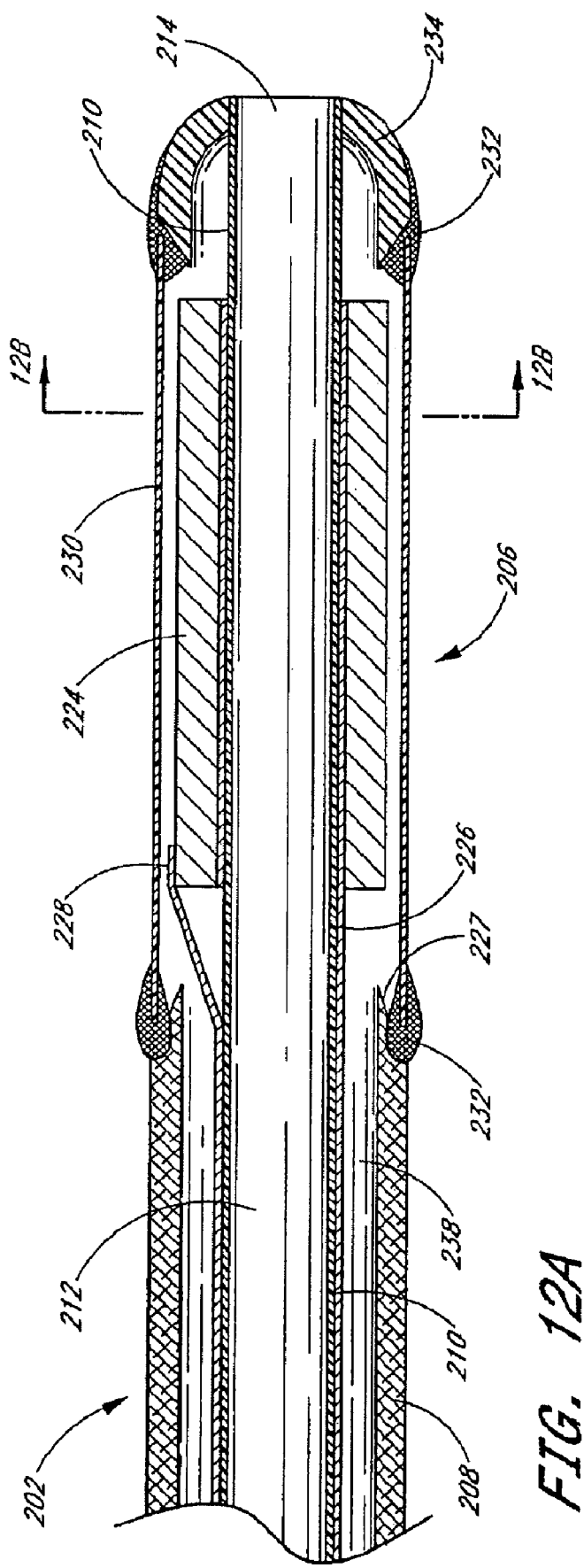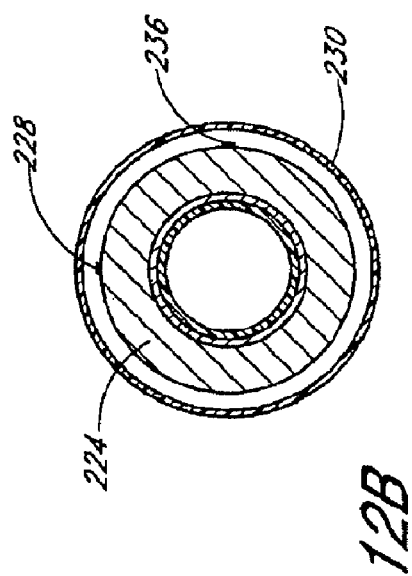
FIG. 12A
FIG. 12B

TREATMENT OF VASCULAR OCCLUSIONS USING ULTRASONIC ENERGY AND MICROBUBBLES

PRIORITY APPLICATION

This application is a continuation of U.S. application Ser. No. 11/046,208 filed Jan. 28, 2005, now U.S. Pat. No. 7,341,569, which claims the benefit of U.S. Provisional Application 60/540,491 filed Jan. 30, 2004, which are hereby incorporated by reference herein in their entirety.

FIELD OF THE INVENTION

The present invention relates generally to treatment of vascular occlusions, and more specifically to treatment of vascular occlusions with ultrasonic energy and a therapeutic compound having microbubbles.

BACKGROUND OF THE INVENTION

Several medical applications use ultrasonic energy. For example, U.S. Pat. Nos. 4,821,740, 4,953,565 and 5,007,438 disclose the use of ultrasonic energy to enhance the effect of various therapeutic compounds. An ultrasonic catheter can be used to deliver ultrasonic energy and a therapeutic compound to a treatment site within a patient's body. Such an ultrasonic catheter typically includes an ultrasound assembly configured to generate ultrasonic energy and a fluid delivery lumen for delivering the therapeutic compound to the treatment site.

As taught in U.S. Pat. No. 6,001,069, ultrasonic catheters can be used to treat human blood vessels that have become partially or completely occluded by plaque, thrombi, emboli or other substances that reduce the blood carrying capacity of the vessel. To remove or reduce the occlusion, the ultrasonic catheter is used to deliver solutions containing therapeutic compounds directly to the occlusion site. Ultrasonic energy generated by the ultrasound assembly enhances the effect of the therapeutic compounds. Such a device can be used in the treatment of diseases such as peripheral arterial occlusion or deep vein thrombosis. In such applications, the ultrasonic energy enhances treatment of the occlusion with therapeutic compounds such as urokinase, tissue plasminogen activator ("tPA"), recombinant tissue plasminogen activator ("rtPA") and the like. Further information on enhancing the effect of a therapeutic compound using ultrasonic energy is provided in U.S. Pat. Nos. 5,318,014, 5,362,309, 5,474,531, 5,628,728, 6,001,069 and 6,210,356.

SUMMARY OF THE INVENTION

Certain therapeutic compounds contain a plurality of microbubbles having, for example, a gas formed therein. The efficacy of a therapeutic compound can be enhanced by the presence of the microbubbles contained therein. The microbubbles act as a nucleus for cavitation, which can help promote the dissolution and removal of a vascular occlusion. Furthermore, the mechanical agitation caused motion of the microbubbles can be effective in mechanically breaking up clot material. Therefore, ultrasound catheter systems configured for use with a microbubble-containing therapeutic compound have been developed.

In one embodiment of the present invention, a method of treating a vascular occlusion located at a treatment site within a patient's vasculature comprises positioning an ultrasound catheter at the treatment site. The method further comprises delivering a microbubble therapeutic compound from the ultrasound catheter to the vascular occlusion during a first treatment phase. The method further comprises pausing the delivery of the microbubble therapeutic compound and delivering ultrasonic energy from the ultrasound catheter to the vascular occlusion during a second treatment phase while the delivery of microbubble therapeutic compound remains paused.

In one embodiment of the present invention, a method of treating a vascular occlusion located at a treatment site within a patient's vasculature comprises passing an ultrasound catheter through the patient's vasculature to the treatment site. The ultrasound catheter includes at least one fluid delivery port. The method further comprises positioning the ultrasound catheter at the treatment site such that the at least one fluid delivery port is positioned within the occlusion. The method further comprises infusing a microbubble therapeutic compound from the ultrasound catheter into an internal portion of the occlusion. The method further comprises pausing delivery of the microbubble therapeutic compound from the ultrasound catheter after a first quantity has been infused into the occlusion. The method further comprises delivering ultrasonic energy from the ultrasound catheter into the infused microbubble therapeutic compound. The method further comprises repositioning the ultrasound catheter at the treatment site. The method further comprises infusing a second quantity of microbubble therapeutic compound from the ultrasound catheter to the treatment site after the ultrasonic energy is delivered to the treatment site.

In one embodiment of the present invention, an ultrasound catheter system comprises an elongate tubular body having an ultrasound radiating member and a fluid delivery lumen positioned therein. The system further comprises a fluid reservoir that is hydraulically coupled to a proximal portion of the fluid delivery lumen. The fluid delivery reservoir contains a microbubble therapeutic compound. The system further comprises an infusion pump configured to pump the microbubble therapeutic compound from the fluid reservoir into the fluid delivery lumen. The system further comprises control circuitry configured to send electrical activation power to the infusion pump and to the ultrasound radiating member. The control circuitry is configured such that the infusion pump and the ultrasound radiating member are not activated simultaneously.

BRIEF DESCRIPTION OF THE DRAWINGS

Exemplary embodiments of the vascular occlusion treatment system are illustrated in the accompanying drawings, which are for illustrative purposes only. The drawings comprise the following figures, in which like numerals indicate like parts.

FIG. 7A is a schematic illustration of the ultrasound assembly of FIG. 5 housed within the inner core of FIG. 4.

FIG. 7B is a cross-sectional view of the ultrasound assembly of FIG. 7A taken along line 7B-7B.

FIG. 7C is a cross-sectional view of the ultrasound assembly of FIG. 7A taken along line 7C-7C.

FIG. 11B is a side view of the distal end of an ultrasonic catheter positioned at the treatment site of FIG. 11A.

FIG. 12A is a cross-sectional view of a distal end of an ultrasonic catheter configured for use within small vessels of a patient's vasculature.

FIG. 12B is a cross-sectional view of the ultrasonic catheter of FIG. 12A taken through line 12B-12B.

DETAILED DESCRIPTION OF PREFERRED EMBODIMENTS

Figure 1:
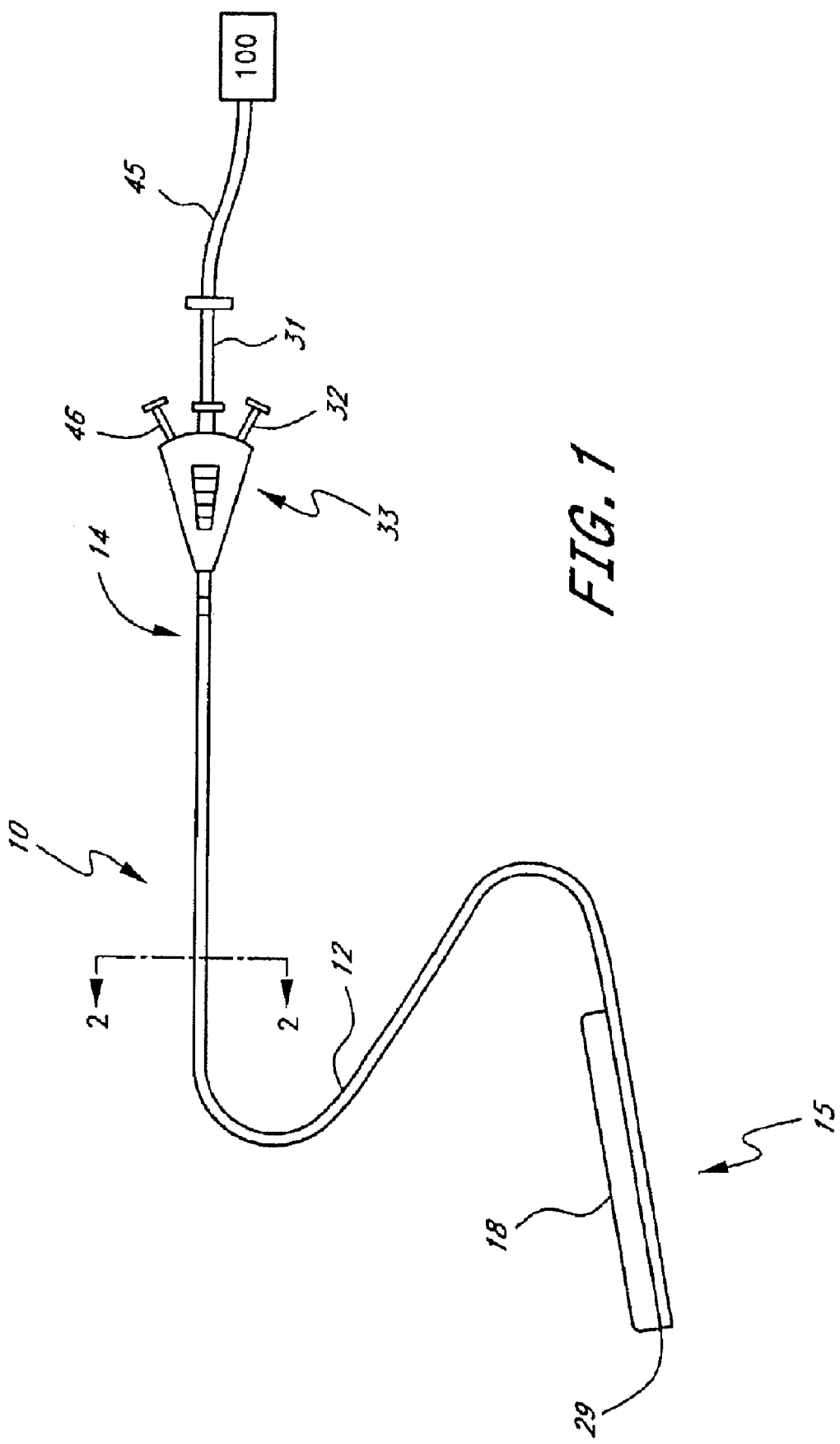
FIG. 1 is a schematic illustration of an ultrasonic catheter configured for insertion into large vessels of the human body.

As set forth above, methods and apparatuses have been developed that allow a vascular occlusion to be treated using both ultrasonic energy and a therapeutic compound having a controlled temperature. Disclosed herein are several exemplary embodiments of ultrasonic catheters that can be used to enhance the efficacy of therapeutic compounds at a treatment site within a patient's body. Also disclosed are exemplary methods for using such catheters. For example, as discussed in greater detail below, the ultrasonic catheters disclosed herein can be used to deliver a therapeutic compound having an elevated temperature, or to heat a therapeutic compound after it has been delivered at a treatment site within the patient's vasculature.

Introduction

As used herein, the term "therapeutic compound" refers broadly, without limitation, and in addition to its ordinary meaning, to a drug, medicament, dissolution compound, genetic material or any other substance capable of effecting physiological functions. Additionally, a mixture includes substances such as these is also encompassed within this definition of "therapeutic compound". Examples of therapeutic compounds include thrombolytic compounds, anti-thrombosis compounds, and other compounds used in the treatment of vascular occlusions, including compounds intended to prevent or reduce clot formation. In applications where human blood vessels that have become partially or completely occluded by plaque, thrombi, emboli or other substances that reduce the blood carrying capacity of a vessel, exemplary therapeutic compounds include, but are not limited to, heparin, urokinase, streptokinase, tPA, rtPA and BB-10153 (manufactured by British Biotech, Oxford, UK).

As used herein, the terms "ultrasonic energy", "ultrasound" and "ultrasonic" refer broadly, without limitation, and in addition to their ordinary meaning, to mechanical energy transferred through longitudinal pressure or compression waves. Ultrasonic energy can be emitted as continuous or pulsed waves, depending on the parameters of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy referred to herein has a frequency between about 20 kHz and about 20 MHz. For example, in one embodiment, the ultrasonic energy has a frequency between about 500 kHz and about 20 MHz. In another embodiment, the ultrasonic energy has a frequency between about 1 MHz and about 3 MHz. In yet another embodiment, the ultrasonic energy has a frequency of about 2 MHz. In certain embodiments described herein, the average acoustic power of the ultrasonic energy is between about 0.01 watts and 300 watts. In one embodiment, the average acoustic power is about 15 watts.

As used herein, the term "ultrasound radiating member" refers broadly, without limitation, and in addition to its ordinary meaning, to any apparatus capable of producing ultrasonic energy. An ultrasonic transducer, which converts electrical energy into ultrasonic energy, is an example of an ultrasound radiating member. An exemplary ultrasonic transducer capable of generating ultrasonic energy from electrical energy is a piezoelectric ceramic oscillator. Piezoelectric ceramics typically comprise a crystalline material, such as quartz, that changes shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating member, and the ultrasonic energy can be transmitted, via, for example, a wire that is coupled to the ultrasound radiating member.

In certain applications, the ultrasonic energy itself provides a therapeutic effect to the patient. Examples of such therapeutic effects include preventing or reducing stenosis and/or restenosis; tissue ablation, abrasion or disruption; promoting temporary or permanent physiological changes in intracellular or intercellular structures; and rupturing micro-balloons or micro-bubbles for therapeutic compound delivery. Further information about such methods can be found in U.S. Pat. Nos. 5,261,291 and 5,431,663.

The ultrasonic catheters described herein can be configured for application of ultrasonic energy over a substantial length of a body lumen, such as, for example, the larger vessels located in the leg. In other embodiments, the ultrasonic catheters described herein can be configured to be inserted into the small cerebral vessels, in solid tissues, in duct systems and in body cavities. Additional embodiments that can be combined with certain features and aspects of the embodiments described herein are described in U.S. patent application Ser. No. 10/291,891, filed 7 Nov. 2002, the entire disclosure of which is hereby incorporated herein by reference.

Overview of a Large Vessel Ultrasonic Catheter.

FIG. 1 schematically illustrates an ultrasonic catheter 10 configured for use in the large vessels of a patient's anatomy. For example, the ultrasonic catheter 10 illustrated in FIG. 1 can be used to treat long segment peripheral arterial occlusions, such as those in the vascular system of the leg.

As illustrated in FIG. 1, the ultrasonic catheter 10 generally includes a multi-component, elongate flexible tubular body 12 having a proximal region 14 and a distal region 15. The tubular body 12 includes a flexible energy delivery section 18 located in the distal region 15. The tubular body 12 and other components of the catheter 10 can be manufactured in accordance with a variety of techniques known to an ordinarily skilled artisan. Suitable materials and dimensions can be readily selected based on the natural and anatomical dimensions of the treatment site and on the desired percutaneous access site.

For example, in an exemplary embodiment, the tubular body proximal region 14 comprises a material that has sufficient flexibility, kink resistance, rigidity and structural support to push the energy delivery section 18 through the patient's vasculature to a treatment site. Examples of such materials include, but are not limited to, extruded polytetrafluoroethylene ("PTFE"), polyethylenes ("PE"), polyamides and other similar materials. In certain embodiments, the tubular body proximal region 14 is reinforced by braiding, mesh or other constructions to provide increased kink resistance and ability to be pushed. For example, nickel titanium or stainless steel wires can be placed along or incorporated into the tubular body 12 to reduce kinking.

For example, in an embodiment configured for treating thrombus in the arteries of the leg, the tubular body 12 has an outside diameter between about 0.060 inches and about 0.075 inches. In another embodiment, the tubular body 12 has an outside diameter of about 0.071 inches. In certain embodiments, the tubular body 12 has an axial length of approximately 105 centimeters, although other lengths can be used in other applications.

In an exemplary embodiment, the tubular body energy delivery section 18 comprises a material that is thinner than the material comprising the tubular body proximal region 14. In another exemplary embodiment, the tubular body energy delivery section 18 comprises a material that has a greater acoustic transparency than the material comprising the tubular body proximal region 14. Thinner materials generally have greater acoustic transparency than thicker materials. Suitable materials for the energy delivery section 18 include, but are not limited to, high or low density polyethylenes, urethanes, nylons, and the like. In certain modified embodiments, the energy delivery section 18 comprises the same material or a material of the same thickness as the proximal region 18.

In an exemplary embodiment, the tubular body 12 is divided into at least three sections of varying stiffness. The first section, which includes the proximal region 14, has a relatively higher stiffness. The second section, which is located in an intermediate region between the proximal region 14 and the distal region 15, has a relatively lower stiffness. This configuration further facilitates movement and placement of the catheter 10. The third section, which includes the energy delivery section 18, has a relatively lower stiffness than the second section in spite of the presence of ultrasound radiating members which can be positioned therein.

Figure 2:
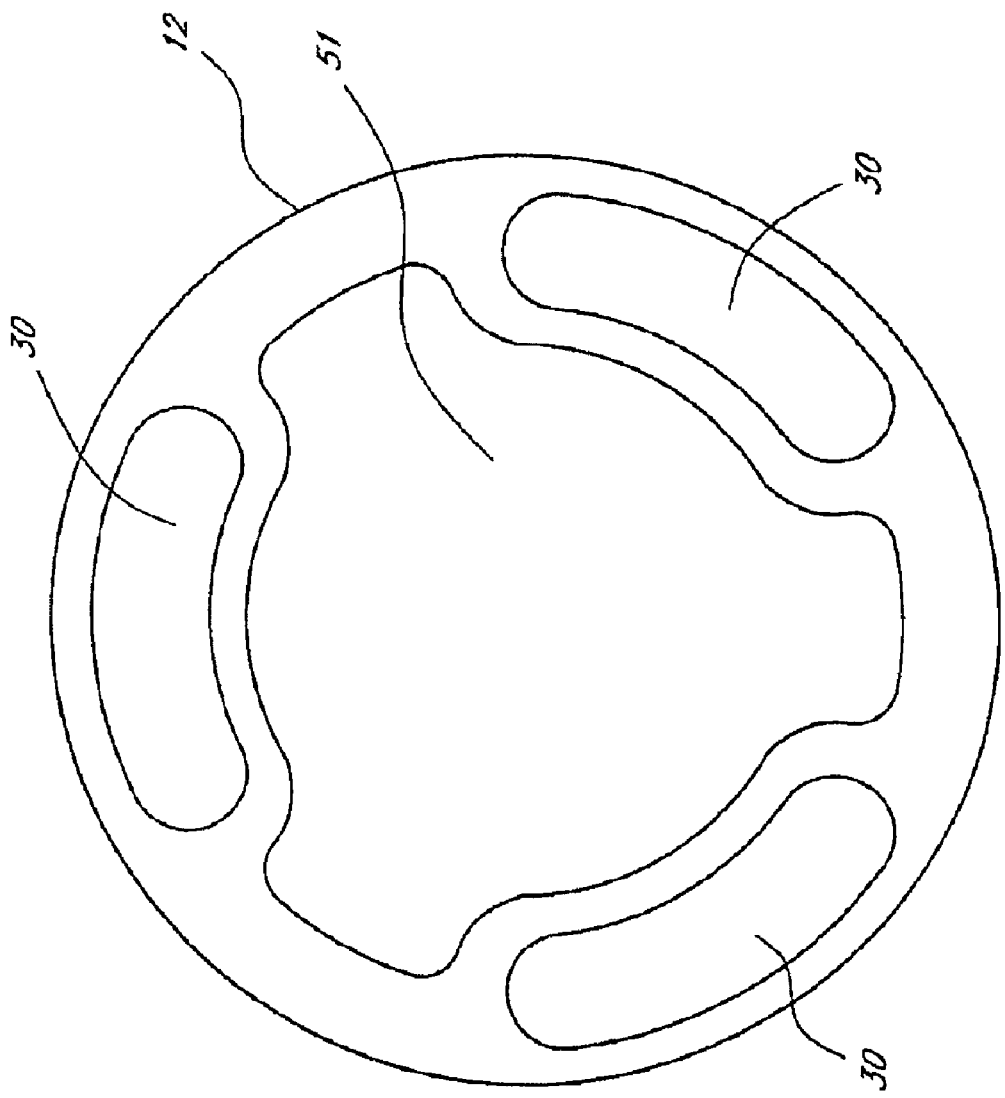
FIG. 2 is a cross-sectional view of the ultrasonic catheter of FIG. 1 taken along line 2-2.

FIG. 2 illustrates a cross section of the tubular body 12 taken along line 2-2 in FIG. 1. In the embodiment illustrated in FIG. 2, three fluid delivery lumens 30 are incorporated into the tubular body 12. In other embodiments, more or fewer fluid delivery lumens can be incorporated into the tubular body 12. In such embodiments, the arrangement of the fluid delivery lumens 30 provides a hollow central lumen 51 passing through the tubular body 12. The cross-section of the tubular body 12, as illustrated in FIG. 2, is substantially constant along the length of the catheter 10. Thus, in such embodiments, substantially the same cross-section is present in both the proximal region 14 and the distal region 15 of the tubular body 12, including the energy delivery section 18.

In certain embodiments, the central lumen 51 has a minimum diameter greater than about 0.030 inches. In another embodiment, the central lumen 51 has a minimum diameter greater than about 0.037 inches. In an exemplary embodiment, the fluid delivery lumens 30 have dimensions of about 0.026 inches wide by about 0.0075 inches high, although other dimensions can be used in other embodiments.

In an exemplary embodiment, the central lumen 51 extends through the length of the tubular body 12. As illustrated in FIG. 1, the central lumen 51 has a distal exit port 29 and a proximal access port 31. The proximal access port 31 forms part of the backend hub 33, which is attached to the tubular body proximal region 14. In such embodiments, the backend hub also includes a cooling fluid fitting 46, which is hydraulically connected to the central lumen 51. In such embodiments, the backend hub 33 also includes a therapeutic compound inlet port 32, which is hydraulically coupled to the fluid delivery lumens 30, and which can also be hydraulically coupled to a source of therapeutic compound via a hub such as a Luer fitting.

Figure 3:
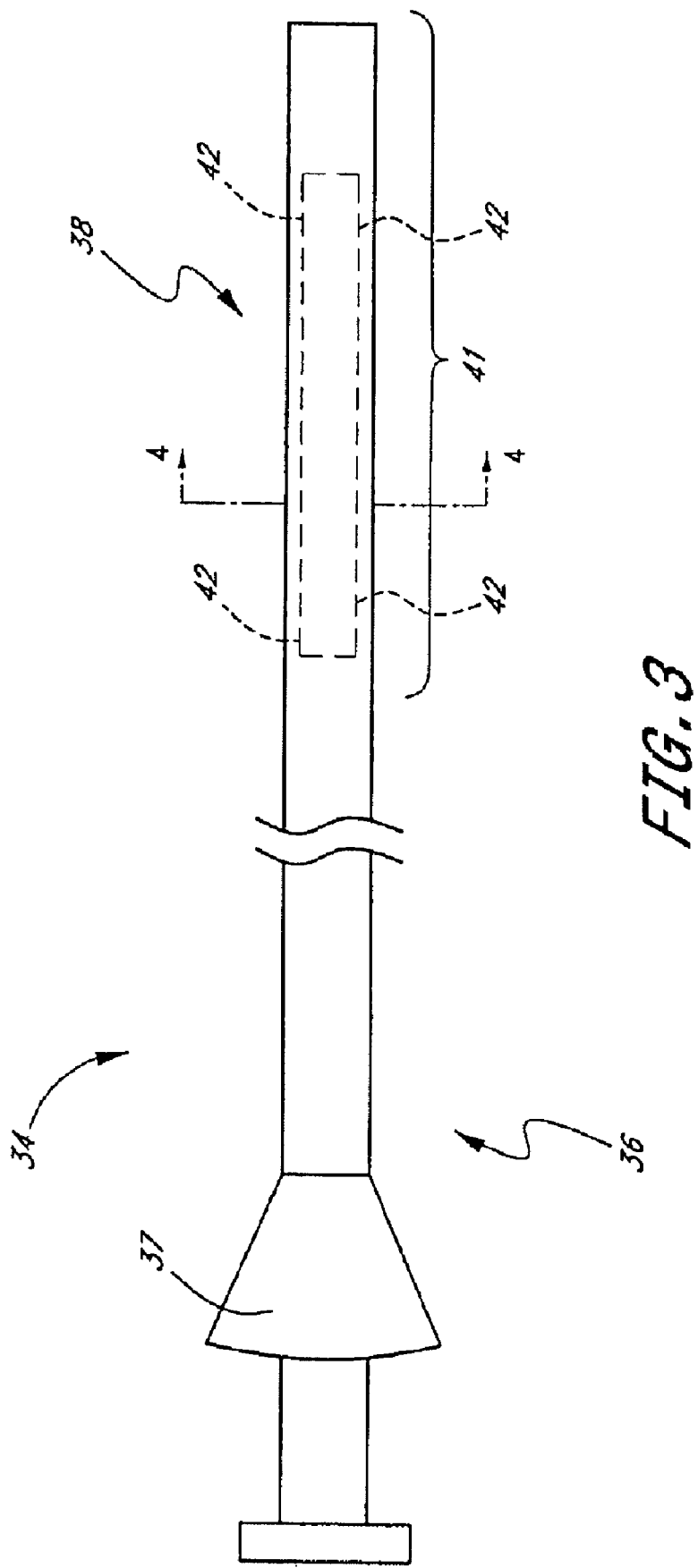
FIG. 3 is a schematic illustration of an elongate inner core configured to be positioned within the central lumen of the catheter illustrated in FIG. 2.

The central lumen 51 is configured to receive an elongate inner core 34, an exemplary embodiment of which is illustrated in FIG. 3. In such embodiments, the elongate inner core 34 includes a proximal region 36 and a distal region 38. A proximal hub 37 is fitted on one end of the inner core proximal region 36. One or more ultrasound radiating members 40 are positioned within an inner core energy delivery section 41 that is located within the distal region 38. The ultrasound radiating members 40 form an ultrasound assembly 42, which will be described in greater detail below.

Figure 4:
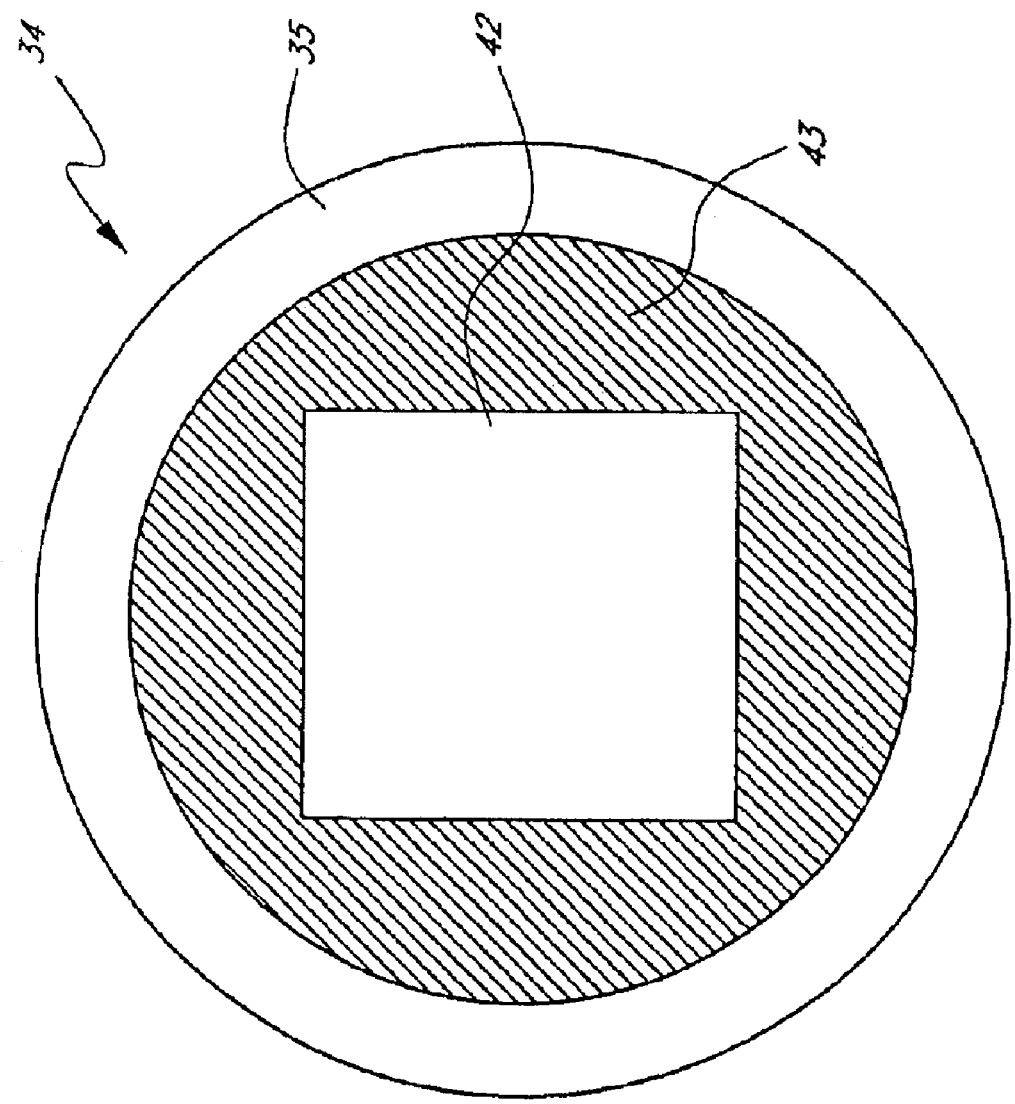
FIG. 4 is a cross-sectional view of the elongate inner core of FIG. 3 taken along line 4-4.

As shown in the cross-section illustrated in FIG. 4, which is taken along lines 4-4 in FIG. 3, in an exemplary embodiment, the inner core 34 has a cylindrical shape, with an outer diameter that permits the inner core 34 to be inserted into the central lumen 51 of the tubular body 12 via the proximal access port 31. Suitable outer diameters of the inner core 34 include, but are not limited to, between about 0.010 inches and about 0.100 inches. In another embodiment, the outer diameter of the inner core 34 is between about 0.020 inches and about 0.080 inches. In yet another embodiment, the inner core 34 has an outer diameter of about 0.035 inches.

Still referring to FIG. 4, the inner core 34 includes a cylindrical outer body 35 that houses the ultrasound assembly 42. The ultrasound assembly 42 includes wiring and ultrasound radiating members, described in greater detail in FIGS. 5 through 7D, such that the ultrasound assembly 42 is capable of radiating ultrasonic energy from the energy delivery section 41 of the inner core 34. The ultrasound assembly 42 is electrically connected to the backend hub 33, where the inner core 34 can be connected to a control system 100 via cable 45 (illustrated in FIG. 1). In an exemplary embodiment, an electrically insulating potting material 43 fills the inner core 34, surrounding the ultrasound assembly 42, thus reducing or preventing movement of the ultrasound assembly 42 with respect to the outer body 35. In one embodiment, the thickness of the outer body 35 is between about 0.0002 inches and 0.010 inches. In another embodiment, the thickness of the outer body 35 is between about 0.0002 inches and 0.005 inches. In yet another embodiment, the thickness of the outer body 35 is about 0.0005 inches.

Figure 5:
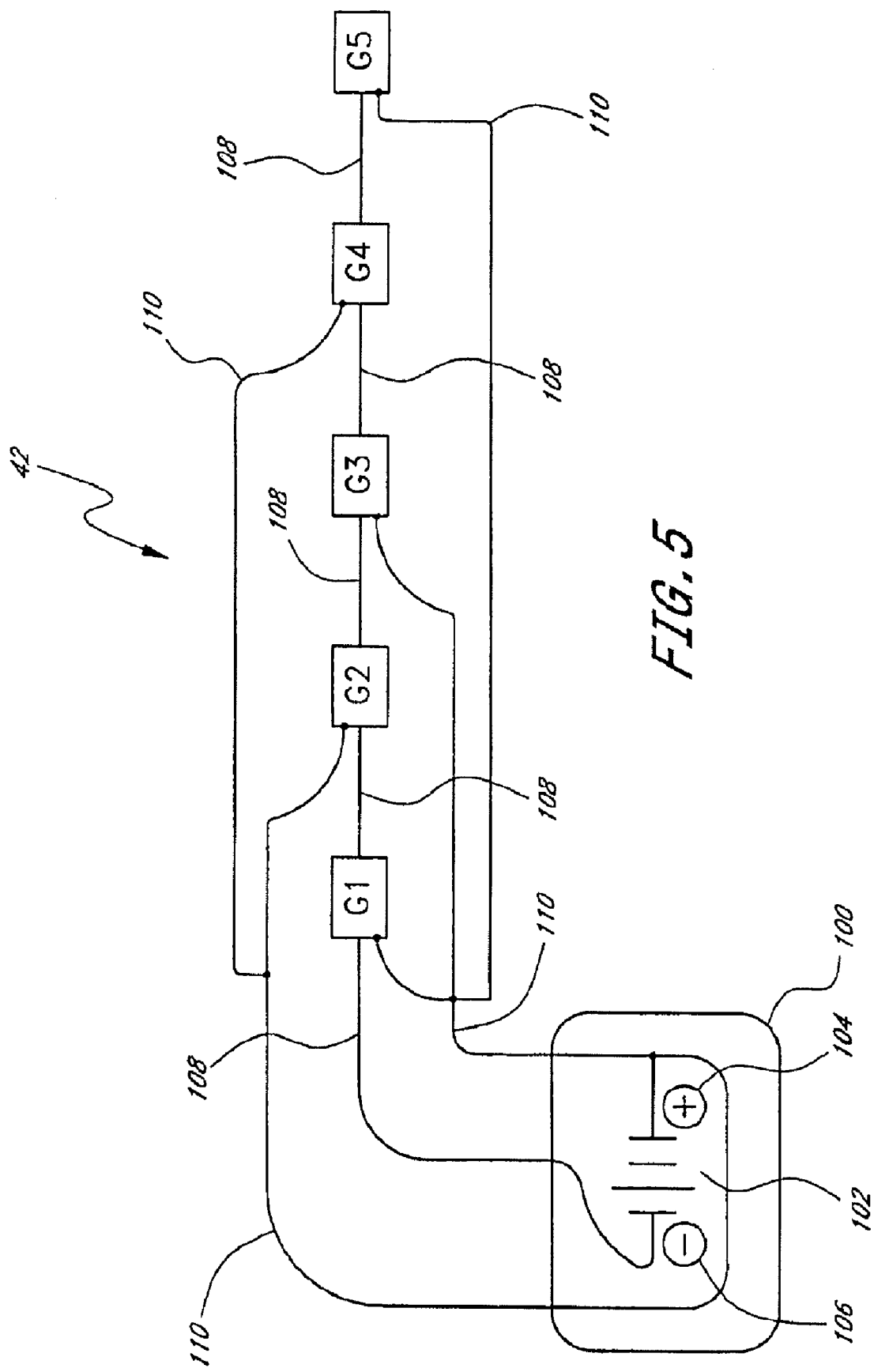
FIG. 5 is a schematic wiring diagram illustrating an exemplary technique for electrically connecting five groups of ultrasound radiating members to form an ultrasound assembly.
Figure 6:
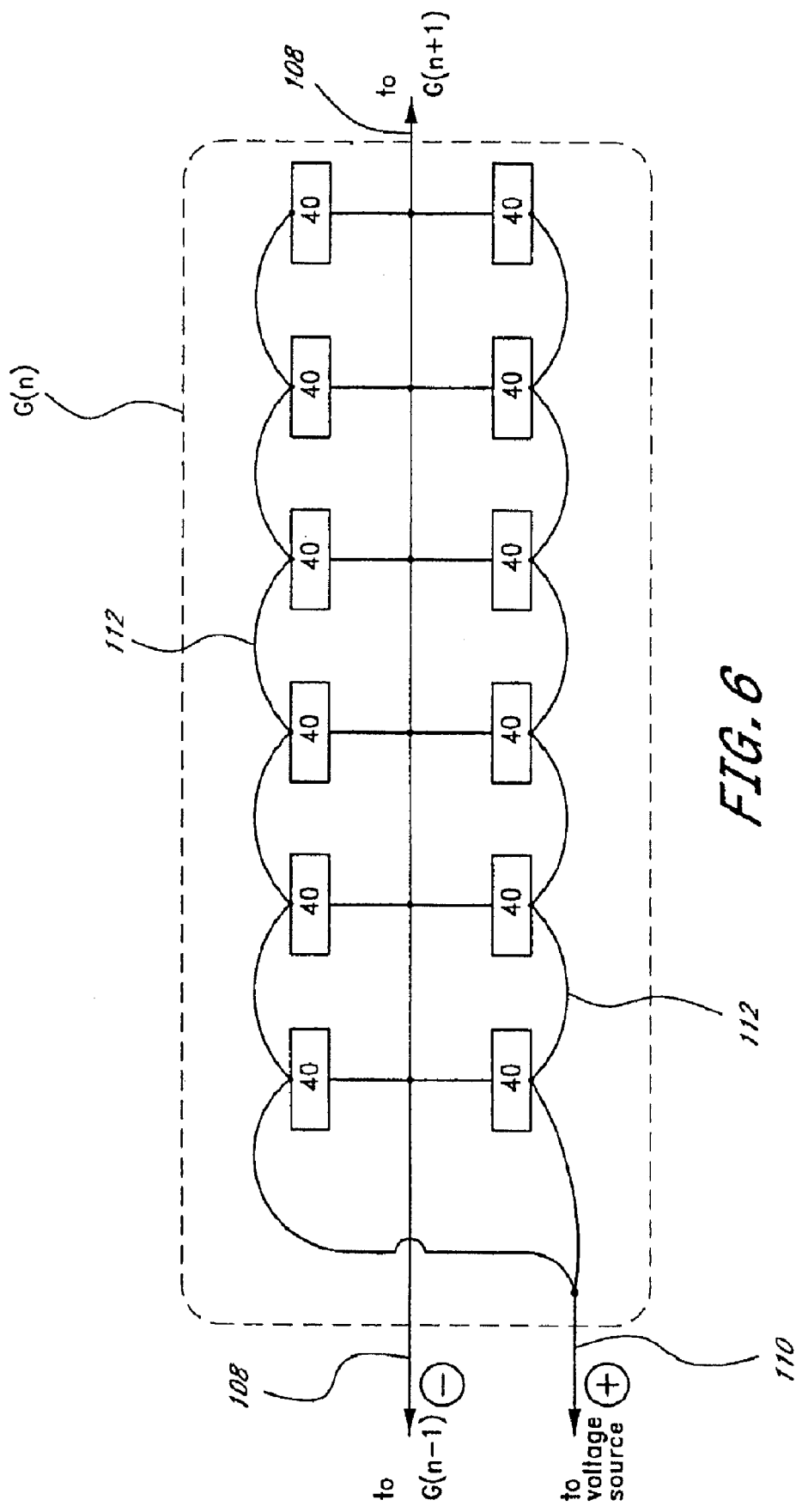
FIG. 6 is a schematic wiring diagram illustrating an exemplary technique for electrically connecting one of the groups of FIG. 5.

In an exemplary embodiment, the ultrasound assembly 42 includes a plurality of ultrasound radiating members 40 that are divided into one or more groups. For example, FIGS. 5 and 6 are schematic wiring diagrams illustrating one technique for connecting five groups of ultrasound radiating members 40 to form the ultrasound assembly 42. As illustrated in FIG. 5, the ultrasound assembly 42 comprises five groups G1, G2, G3, G4, G5 of ultrasound radiating members 40 that are electrically connected to each other. The five groups are also electrically connected to the control system 100.

Still referring to FIG. 5, in an exemplary embodiment, the control circuitry 100 includes a voltage source 102 having a positive terminal 104 and a negative terminal 106. The negative terminal 106 is connected to common wire 108, which connects the five groups G1-G5 of ultrasound radiating members 40 in series. The positive terminal 104 is connected to a plurality of lead wires 110, which each connect to one of the five groups G1-G5 of ultrasound radiating members 40. Thus, under this configuration, each of the five groups G1-G5, one of which is illustrated in FIG. 6, is connected to the positive terminal 104 via one of the lead wires 110, and to the negative terminal 106 via the common wire 108.

Referring now to FIG. 6, each group G1-G5 includes a plurality of ultrasound radiating members 40. Each of the ultrasound radiating members 40 is electrically connected to the common wire 108 and to the lead wire 110 via a positive contact wires 112. Thus, when wired as illustrated, a substantially constant voltage difference will be applied to each ultrasound radiating member 40 in the group. Although the group illustrated in FIG. 6 includes twelve ultrasound radiating members 40, in other embodiments, more or fewer ultrasound radiating members 40 can be included in the group. Likewise, more or fewer than five groups can be included within the ultrasound assembly 42 illustrated in FIG. 5.

FIG. 7A illustrates an exemplary technique for arranging the components of the ultrasound assembly 42 (as schematically illustrated in FIG. 5) into the inner core 34 (as schematically illustrated in FIG. 4). FIG. 7A is a cross-sectional view of the ultrasound assembly 42 taken within group G1 in FIG. 5, as indicated by the presence of four lead wires 110. For example, if a cross-sectional view of the ultrasound assembly 42 was taken within group G4 in FIG. 5, only one lead wire 110 would be present (that is, the one lead wire connecting group G5).

In the exemplary embodiment illustrated in FIG. 7A, the common wire 108 includes an elongate, flat piece of electrically conductive material in electrical contact with a pair of ultrasound radiating members 40. Each of the ultrasound radiating members 40 is also in electrical contact with a positive contact wire 112. Because the common wire 108 is connected to the negative terminal 106, and the positive contact wire 112 is connected to the positive terminal 104, a voltage difference can be created across each ultrasound radiating member 40. In such embodiments, lead wires 110 are separated from the other components of the ultrasound assembly 42, thus preventing interference with the operation of the ultrasound radiating members 40 as described above. For example, in an exemplary embodiment, the inner core 34 is filled with an insulating potting material 43, thus deterring unwanted electrical contact between the various components of the ultrasound assembly 42.

FIGS. 7B and 7C illustrate cross sectional views of the inner core 34 of FIG. 7A taken along lines 7B-7B and 7C-7C, respectively. As illustrated in FIG. 7B, the ultrasound radiating members 40 are mounted in pairs along the common wire 108. The ultrasound radiating members 40 are connected by positive contact wires 112, such that substantially the same voltage is applied to each ultrasound radiating member 40. As illustrated in FIG. 7C, the common wire 108 includes wide regions 108W upon which the ultrasound radiating members 40 can be mounted, thus reducing the likelihood that the paired ultrasound radiating members 40 will short together. In certain embodiments, outside the wide regions 108W, the common wire 108 can have a more conventional, rounded wire shape.

Figure 7D:
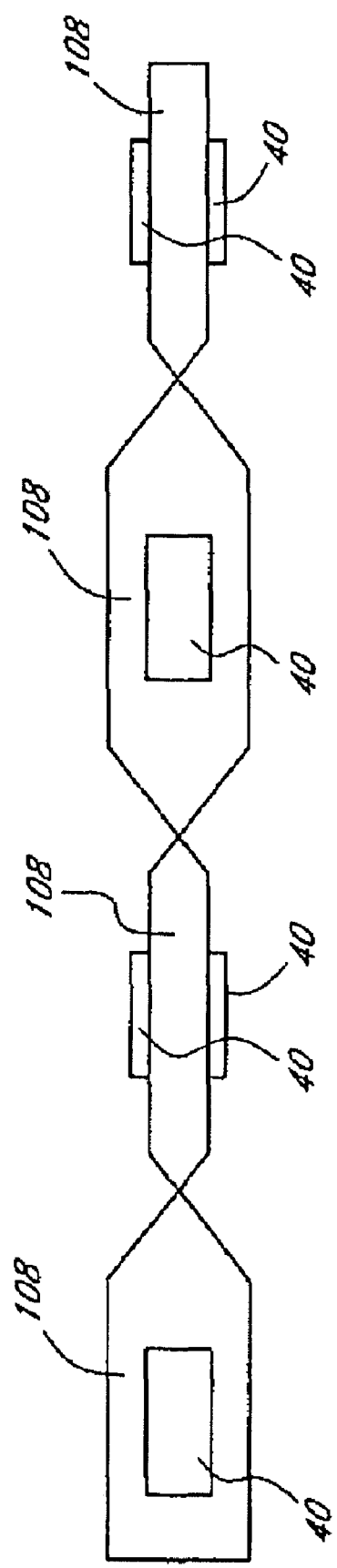
FIG. 7D is a side view of an ultrasound assembly center wire twisted into a helical configuration.

In a modified embodiment, such as illustrated in FIG. 7D, the common wire 108 is twisted to form a helical shape before being fixed within the inner core 34. In such embodiments, the ultrasound radiating members 40 are oriented in a plurality of radial directions, thus enhancing the radial uniformity of the resulting ultrasonic energy field.

The wiring arrangement described above can be modified to allow each group G1, G2, G3, G4, G5 to be independently powered. Specifically, by providing a separate power source within the control system 100 for each group, each group can be individually turned on or off, or can be driven at an individualized power level. This advantageously allows the delivery of ultrasonic energy to be "turned off" in regions of the treatment site where treatment is complete, thus preventing deleterious or unnecessary ultrasonic energy to be applied to the patient.

The embodiments described above, and illustrated in FIGS. 5 through 7, include a plurality of ultrasound radiating members grouped spatially. That is, in such embodiments, the ultrasound radiating members within a certain group are positioned adjacent to each other, such that when a single group is activated, ultrasonic energy is delivered from a certain length of the ultrasound assembly. However, in modified embodiments, the ultrasound radiating members of a certain group may be spaced apart from each other, such that the ultrasound radiating members within a certain group are not positioned adjacent to each other. In such embodiments, when a single group is activated, ultrasonic energy can be delivered from a larger, spaced apart portion of the ultrasound assembly. Such modified embodiments can be advantageous in applications where a less focussed, more diffuse ultrasonic energy field is to be delivered to the treatment site.

In an exemplary embodiment, the ultrasound radiating members 40 comprise rectangular lead zirconate titanate ("PZT") ultrasound transducers that have dimensions of about 0.017 inches by about 0.010 inches by about 0.080 inches. In other embodiments, other configurations and dimensions can be used. For example, disc-shaped ultrasound radiating members 40 can be used in other embodiments. In an exemplary embodiment, the common wire 108 comprises copper, and is about 0.005 inches thick, although other electrically conductive materials and other dimensions can be used in other embodiments. In an exemplary embodiment, lead wires 110 are 36 gauge electrical conductors, and positive contact wires 112 are 42 gauge electrical conductors. However, other wire gauges can be used in other embodiments.

As described above, suitable frequencies for the ultrasound radiating members 40 include, but are not limited to, from about 20 kHz to about 20 MHz. In one embodiment, the frequency is between about 500 kHz and about 20 MHz, and in another embodiment the frequency is between about 1 MHz and about 3 MHz. In yet another embodiment, the ultrasound radiating members 40 are operated with a frequency of about 2 MHz.

Figure 8:
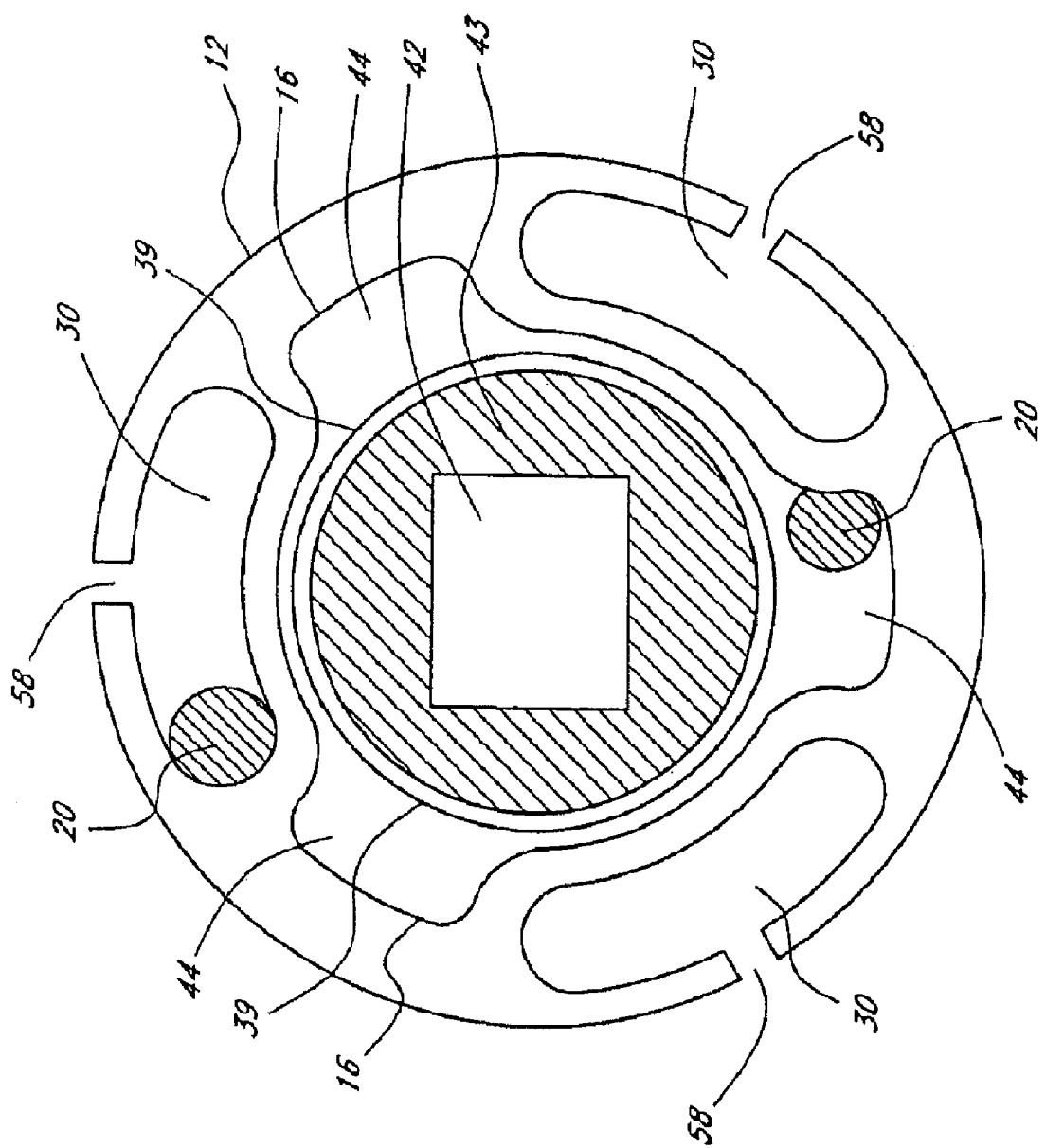
FIG. 8 illustrates the energy delivery section of the inner core of FIG. 4 positioned within the energy delivery section of the tubular body of FIG. 2.

FIG. 8 illustrates the inner core 34 positioned within the tubular body 12. Details of the ultrasound assembly 42, provided in FIG. 7A, are omitted for clarity. As described above, the inner core 34 can be slid within the central lumen 51 of the tubular body 12, thereby allowing the inner core energy delivery section 41 to be positioned within the tubular body energy delivery section 18. For example, in an exemplary embodiment, the materials comprising the inner core energy delivery section 41, the tubular body energy delivery section 18, and the potting material 43 all comprise materials having a similar acoustic impedance, thereby minimizing ultrasonic energy losses across material interfaces.

FIG. 8 further illustrates placement of fluid delivery ports 58 within the tubular body energy delivery section 18. As illustrated, holes or slits are formed from the fluid delivery lumen 30 through the tubular body 12, thereby permitting fluid flow from the fluid delivery lumen 30 to the treatment site. A plurality of fluid delivery ports 58 can be positioned axially along the tubular body 12. Thus, a source of therapeutic compound coupled to the inlet port 32 provides a hydraulic pressure which drives the therapeutic compound through the fluid delivery lumens 30 and out the fluid delivery ports 58.

By spacing the fluid delivery lumens 30 around the circumference of the tubular body 12 substantially evenly, as illustrated in FIG. 8, a substantially uniform flow of therapeutic compound around the circumference of the tubular body 12 can be achieved. Additionally, the size, location and geometry of the fluid delivery ports 58 can be selected to provide uniform fluid flow from the fluid delivery ports 30 to the treatment site. For example, in one embodiment, fluid delivery ports closer to the proximal region of the energy delivery section 18 have smaller diameters than fluid delivery ports closer to the distal region of the energy delivery section 18, thereby allowing uniform delivery of therapeutic compound in the energy delivery section.

For example, in one embodiment in which the fluid delivery ports 58 have similar sizes along the length of the tubular body 12, the fluid delivery ports 58 have a diameter between about 0.0005 inches to about 0.0050 inches. In another embodiment in which the size of the fluid delivery ports 58 changes along the length of the tubular body 12, the fluid delivery ports 58 have a diameter between about 0.001 inches to about 0.005 inches in the proximal region of the energy delivery section 18, and between about 0.005 inches to about 0.0020 inches in the distal region of the energy delivery section 18. The increase in size between adjacent fluid delivery ports 58 depends on a variety of factors, including the material comprising the tubular body 12, and on the size of the fluid delivery lumen 30. The fluid delivery ports 58 can be created in the tubular body 12 by punching, drilling, burning or ablating (such as with a laser), or by other suitable methods. Therapeutic compound flow along the length of the tubular body 12 can also be increased by increasing the density of the fluid delivery ports 58 toward the distal region of the energy delivery section.

In certain applications, a spatially nonuniform flow of therapeutic compound from the fluid delivery ports 58 to the treatment site is to be provided. In such applications, the size, location and geometry of the fluid delivery ports 58 can be selected to provide such nonuniform fluid flow.

Referring still to FIG. 8, placement of the inner core 34 within the tubular body 12 further defines cooling fluid lumens 44. Cooling fluid lumens 44 are formed between an outer surface 39 of the inner core 34 and an inner surface 16 of the tubular body 12. In certain embodiments, a cooling fluid is introduced through the proximal access port 31 such that cooling fluid flows through cooling fluid lumens 44 and out of the catheter 10 through distal exit port 29 (see FIG. 1). In an exemplary embodiment, the cooling fluid lumens 44 are substantially evenly spaced around the circumference of the tubular body 12 (that is, at approximately 120° increments for a three-lumen configuration), thereby providing substantially uniform cooling fluid flow over the inner core 34. Such a configuration advantageously removes thermal energy from the treatment site. As will be explained below, the flow rate of the cooling fluid and the power to the ultrasound assembly 42 can be adjusted to maintain the temperature of the inner core energy delivery section 41, or of the treatment site generally, within a desired range.

In an exemplary embodiment, the inner core 34 can be rotated or moved within the tubular body 12. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the tubular body 12 without kinking of the tubular body 12. Additionally, in an exemplary embodiment, the inner core outer body 35 comprises a material having the ability to transmit torque. Suitable materials for the inner core outer body 35 include, but are not limited to, polyimides, polyesters, polyurethanes, thermoplastic elastomers and braided polyimides.

In an exemplary embodiment, the fluid delivery lumens 30 and the cooling fluid lumens 44 are open at the distal end of the tubular body 12, thereby allowing the therapeutic compound and the cooling fluid to pass into the patient's vasculature at the distal exit port 29. In a modified embodiment, the fluid delivery lumens 30 can be selectively occluded at the distal end of the tubular body 12, thereby providing additional hydraulic pressure to drive the therapeutic compound out of the fluid delivery ports 58. In either configuration, the inner core 34 can be prevented from passing through the distal exit port 29 by providing the inner core 34 with a length that is less than the length of the tubular body 12. In other embodiments, a protrusion is formed within the tubular body 12 in the distal region 15, thereby preventing the inner core 34 from passing through the distal exit port 29.

In other embodiments, the catheter 10 includes an occlusion device positioned at the distal exit port 29. In such embodiments, the occlusion device has a reduced inner diameter that can accommodate a guidewire, but that is less than the inner diameter of the central lumen 51. Thus, the inner core 34 is prevented from extending past the occlusion device and out the distal exit port 29. For example, suitable inner diameters for the occlusion device include, but are not limited to, between about 0.005 inches and about 0.050 inches. In other embodiments, the occlusion device has a closed end, thus preventing cooling fluid from leaving the catheter 10, and instead recirculating to the tubular body proximal region 14. These and other cooling fluid flow configurations permit the power provided to the ultrasound assembly 42 to be increased in proportion to the cooling fluid flow rate. Additionally, certain cooling fluid flow configurations can reduce exposure of the patient's body to cooling fluids.

In an exemplary embodiment, such as illustrated in FIG. 8, the tubular body 12 includes one or more temperature sensors 20 that are positioned within the energy delivery section 18. In such embodiments, the tubular body proximal region 14 includes a temperature sensor lead which can be incorporated into cable 45 (illustrated in FIG. 1). Suitable temperature sensors include, but are not limited to, temperature sensing diodes, thermistors, thermocouples, resistance temperature detectors ("RTDs") and fiber optic temperature sensors which use thermalchromic liquid crystals. Suitable temperature sensor 20 geometries include, but are not limited to, a point, a patch or a stripe. The temperature sensors 20 can be positioned within one or more of the fluid delivery lumens 30, and/or within one or more of the cooling fluid lumens 44.

Figure 9:
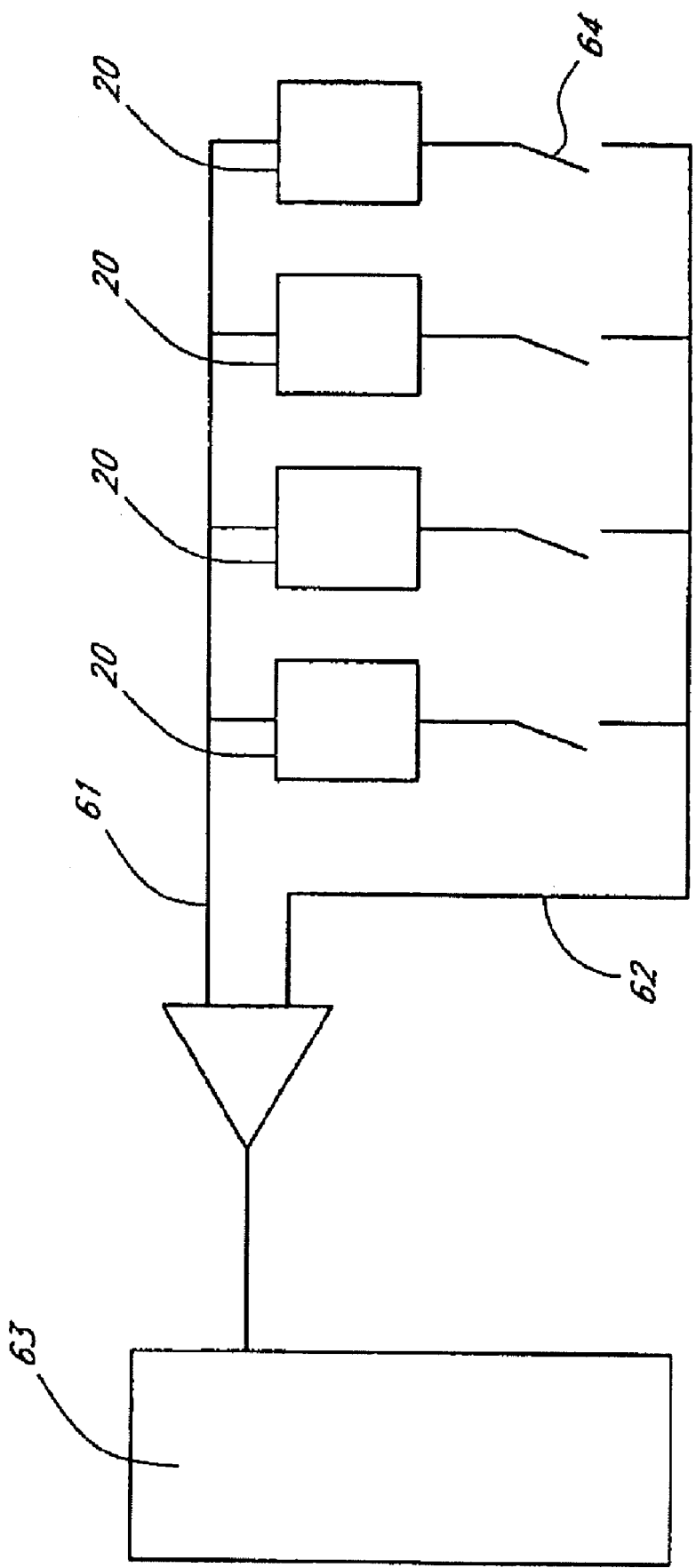
FIG. 9 illustrates a wiring diagram for connecting a plurality of temperature sensors with a common wire.

FIG. 9 illustrates an exemplary embodiment for electrically connecting the temperature sensors 20. In such embodiments, each temperature sensor 20 is coupled to a common wire 61 and is associated with an individual return wire 62. Accordingly, n+1 wires are passed through the tubular body 12 to independently sense the temperature at n temperature sensors 20. The temperature at a selected temperature sensor 20 can be determined by closing a switch 64 to complete a circuit between the return wire 62 associated with the selected thermocouple and the common wire 61. In embodiments wherein the temperature sensors 20 are thermocouples, the temperature can be calculated from the voltage in the circuit using, for example, a sensing circuit 63, which can be located within the external control circuitry 100.

In other embodiments, the temperature sensors 20 can be independently wired. In such embodiments, 2n wires are passed through the tubular body 12 to independently sense the temperature at n temperature sensors 20. In still other embodiments, the flexibility of the tubular body 12 can be improved by using fiber optic based temperature sensors 20. In such embodiments, flexibility can be improved because only n fiber optic members are used to sense the temperature at n independent temperature sensors 20.

Figure 10:
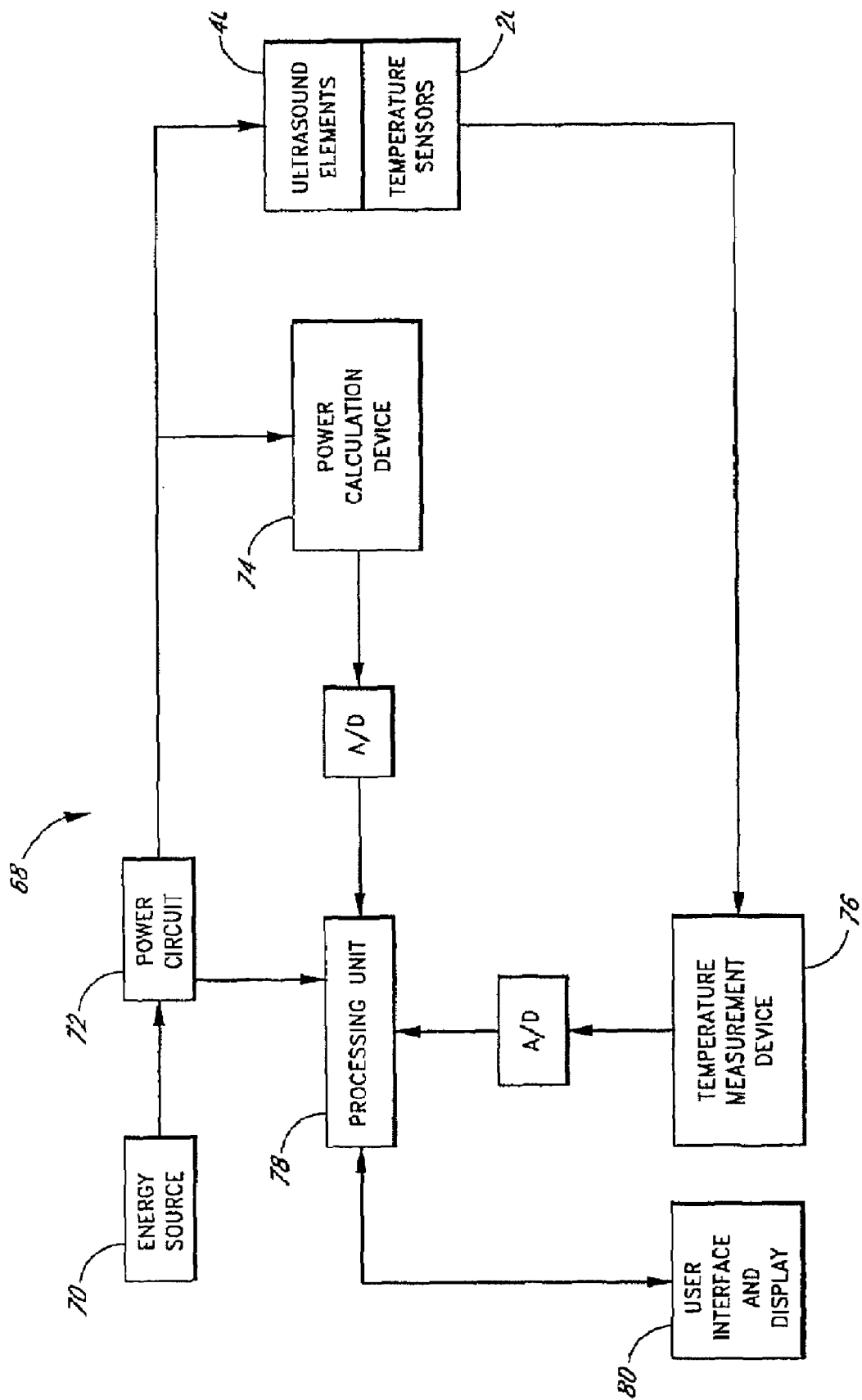
FIG. 10 is a block diagram of a feedback control system for use with an ultrasonic catheter.

FIG. 10 schematically illustrates one embodiment of a feedback control system 68 that can be used with the catheter 10. The feedback control system 68 can be integrated into the control system 100 that is connected to the inner core 34 via cable 45 (as illustrated in FIG. 1). The feedback control system 68 allows the temperature at each temperature sensor 20 to be monitored and allows the output power of the energy source 70 to be adjusted accordingly. A physician can, if desired, override the closed or open loop system.

In an exemplary embodiment, the feedback control system 68 includes an energy source 70, power circuits 72 and a power calculation device 74 that is coupled to the ultrasound radiating members 40. A temperature measurement device 76 is coupled to the temperature sensors 20 in the tubular body 12. A processing unit 78 is coupled to the power calculation device 74, the power circuits 72 and a user interface and display 80.

In an exemplary method of operation, the temperature at each temperature sensor 20 is determined by the temperature measurement device 76. The processing unit 78 receives each determined temperature from the temperature measurement device 76. The determined temperature can then be displayed to the user at the user interface and display 80.

In an exemplary embodiment, the processing unit 78 includes logic for generating a temperature control signal. The temperature control signal is proportional to the difference between the measured temperature and a desired temperature. The desired temperature can be determined by the user (as set at the user interface and display 80) or can be preset within the processing unit 78.

In such embodiments, the temperature control signal is received by the power circuits 72. The power circuits 72 are configured to adjust the power level, voltage, phase and/or current of the electrical energy supplied to the ultrasound radiating members 40 from the energy source 70. For example, when the temperature control signal is above a particular level, the power supplied to a particular group of ultrasound radiating members 40 is reduced in response to that temperature control signal. Similarly, when the temperature control signal is below a particular level, the power supplied to a particular group of ultrasound radiating members 40 is increased in response to that temperature control signal. After each power adjustment, the processing unit 78 monitors the temperature sensors 20 and produces another temperature control signal which is received by the power circuits 72.

In an exemplary embodiment, the processing unit 78 optionally includes safety control logic. The safety control logic detects when the temperature at a temperature sensor 20 exceeds a safety threshold. In this case, the processing unit 78 can be configured to provide a temperature control signal which causes the power circuits 72 to stop the delivery of energy from the energy source 70 to that particular group of ultrasound radiating members 40.

Because, in certain embodiments, the ultrasound radiating members 40 are mobile relative to the temperature sensors 20, it can be unclear which group of ultrasound radiating members 40 should have a power, voltage, phase and/or current level adjustment. Consequently, each group of ultrasound radiating members 40 can be identically adjusted in certain embodiments. For example, in a modified embodiment, the power, voltage, phase, and/or current supplied to each group of ultrasound radiating members 40 is adjusted in response to the temperature sensor 20 which indicates the highest temperature. Making voltage, phase and/or current adjustments in response to the temperature sensed by the temperature sensor 20 indicating the highest temperature can reduce overheating of the treatment site.

The processing unit 78 can also be configured to receive a power signal from the power calculation device 74. The power signal can be used to determine the power being received by each group of ultrasound radiating members 40. The determined power can then be displayed to the user on the user interface and display 80.

As described above, the feedback control system 68 can be configured to maintain tissue adjacent to the energy delivery section 18 below a desired temperature. For example, in certain applications, tissue at the treatment site is to have a temperature increase of less than or equal to approximately 6° C. As described above, the ultrasound radiating members 40 can be electrically connected such that each group of ultrasound radiating members 40 generates an independent output. In certain embodiments, the output from the power circuit maintains a selected energy for each group of ultrasound radiating members 40 for a selected length of time.

The processing unit 78 can comprise a digital or analog controller, such as a computer with software. In embodiments wherein the processing unit 78 is a computer, the computer can include a central processing unit ("CPU") coupled through a system bus. In such embodiments, the user interface and display 80 can include a mouse, a keyboard, a disk drive, a display monitor, a nonvolatile memory system, and/or other computer components. In an exemplary embodiment, program memory and/or data memory is also coupled to the bus.

In another embodiment, in lieu of the series of power adjustments described above, a profile of the power to be delivered to each group of ultrasound radiating members 40 can be incorporated into the processing unit 78, such that a preset amount of ultrasonic energy to be delivered is preprofiled. In such embodiments, the power delivered to each group of ultrasound radiating members 40 is provided according to the preset profiles.

In an exemplary embodiment, the ultrasound radiating members are operated in a pulsed mode. For example, in one embodiment, the time average power supplied to the ultrasound radiating members is between about 0.1 watts and about 2 watts. In another embodiment, the time average power supplied to the ultrasound radiating members is between about 0.5 watts and about 1.5 watts. In yet another embodiment, the time average power supplied to the ultrasound radiating members is approximately 0.6 watts or approximately 1.2 watts. In an exemplary embodiment, the duty cycle is between about 1% and about 50%. In another embodiment, the duty cycle is between about 5% and about 25%. In yet another embodiment, the duty cycles is approximately 7.5% or approximately 15%. In an exemplary embodiment, the pulse averaged power is between about 0.1 watts and about 20 watts. In another embodiment, the pulse averaged power is between approximately 5 watts and approximately 20 watts. In yet another embodiment, the pulse averaged power is approximately 8 watts or approximately 16 watts. The amplitude during each pulse can be constant or varied.

In an exemplary embodiment, the pulse repetition rate is between about 5 Hz and about 150 Hz. In another embodiment, the pulse repetition rate is between about 10 Hz and about 50 Hz. In yet another embodiment, the pulse repetition rate is approximately 30 Hz. In an exemplary embodiment, the pulse duration is between about 1 millisecond and about 50 milliseconds. In another embodiment, the pulse duration is between about 1 millisecond and about 25 milliseconds. In yet another embodiment, the pulse duration is approximately 2.5 milliseconds or approximately 5 milliseconds.

For example, in one particular embodiment, the ultrasound radiating members are operated at an average power of approximately 0.6 watts, a duty cycle of approximately 7.5%, a pulse repetition rate of approximately 30 Hz, a pulse average electrical power of approximately 8 watts and a pulse duration of approximately 2.5 milliseconds.

In an exemplary embodiment, the ultrasound radiating member used with the electrical parameters described herein has an acoustic efficiency greater than approximately 50%. In another embodiment, the ultrasound radiating member used with the electrical parameters described herein has an acoustic efficiency greater than approximately 75%. As described herein, the ultrasound radiating members can be formed in a variety of shapes, such as, cylindrical (solid or hollow), flat, bar, triangular, and the like. In an exemplary embodiment, the length of the ultrasound radiating member is between about 0.1 cm and about 0.5 cm, and the thickness or diameter of the ultrasound radiating member is between about 0.02 cm and about 0.2 cm.

Figure 11A:
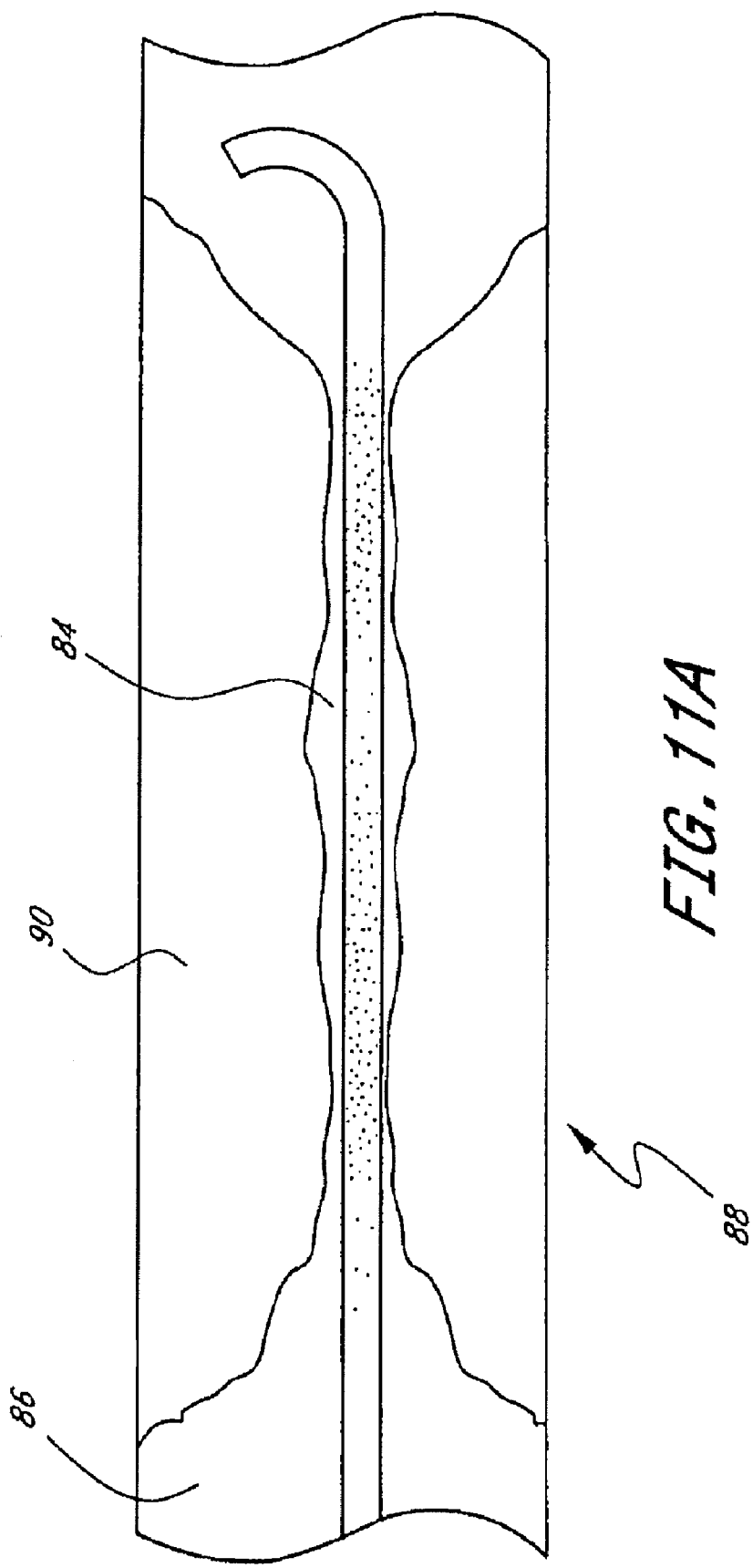
FIG. 11A is a side view of a treatment site.
Figure 11C:
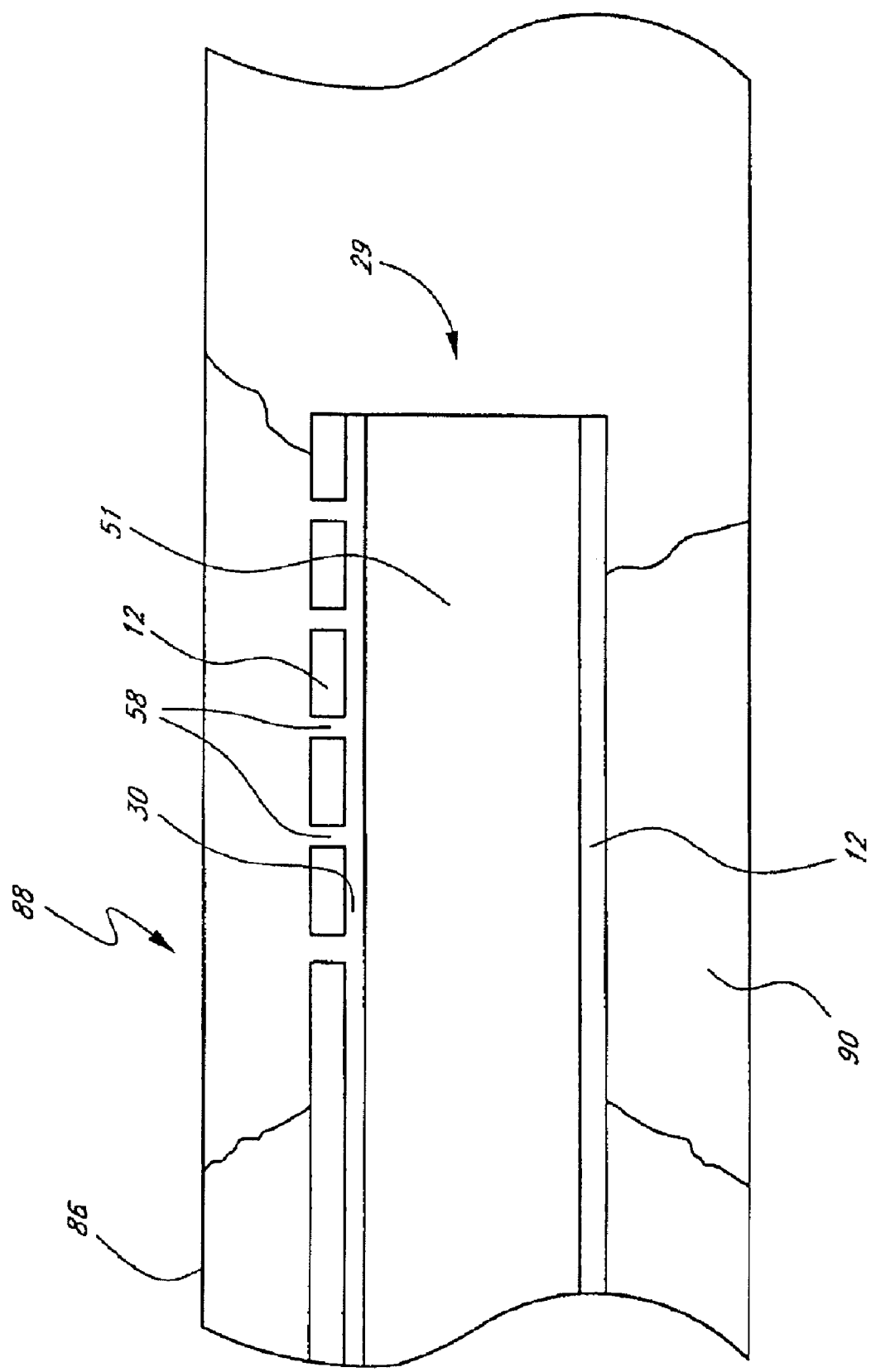
FIG. 11C is a cross-sectional view of the distal end of the ultrasonic catheter of FIG. 11B positioned at the treatment site before a treatment.

FIGS. 11A through 11D illustrate an exemplary method for using certain embodiments of the ultrasonic catheter 10 describe herein. As illustrated in FIG. 11A, a guidewire 84 similar to a guidewire used in typical angioplasty procedures is directed through a patient's vessels 86 to a treatment site 88 that includes a clot 90. The guidewire 84 is optionally directed through the clot 90. Suitable vessels 86 include, but are not limited to, the large periphery blood vessels of the body. Additionally, as mentioned above, the ultrasonic catheter 10 also has utility in various imaging applications or in applications for treating and/or diagnosing other diseases in other body parts.

As illustrated in FIG. 11B, the tubular body 12 is slid over and is advanced along the guidewire 84, for example using conventional over-the-guidewire techniques. The tubular body 12 is advanced until the energy delivery section 18 is positioned at the clot 90. In certain embodiments, radiopaque markers (not shown) are optionally positioned along the tubular body energy delivery section 18 to aid in the positioning of the tubular body 12 within the treatment site 88.

As illustrated in FIG. 10C, after the tubular body 12 is delivered to the treatment site 88, the guidewire 84 is withdrawn from the tubular body 12 by pulling the guidewire 84 from the proximal region 14 of the catheter 10 while holding the tubular body 12 stationary. This leaves the tubular body 12 positioned at the treatment site 88.

As illustrated in FIG. 10D, the inner core 34 is then inserted into the tubular body 12 until the ultrasound assembly 42 is positioned at least partially within the energy delivery section 18. In one embodiment, the ultrasound assembly 42 can be configured to be positioned at least partially within the energy delivery section 18 when the inner core 24 abuts the occlusion device at the distal end of the tubular body 12. Once the inner core 34 is positioned in such that the ultrasound assembly 42 is at least partially within the energy delivery section, the ultrasound assembly 42 is activated to deliver ultrasonic energy to the clot 90. As described above, in one embodiment, ultrasonic energy having a frequency between about 20 kHz and about 20 MHz is delivered to the treatment site.

In an exemplary embodiment, the ultrasound assembly 42 includes sixty ultrasound radiating members 40 spaced over a length of approximately 30 to approximately 50 cm. In such embodiments, the catheter 10 can be used to treat an elongate clot 90 without requiring moving or repositioning the catheter 10 during the treatment. However, in modified embodiments, the inner core 34 can be moved or rotated within the tubular body 12 during the treatment. Such movement can be accomplished by maneuvering the proximal hub 37 of the inner core 34 while holding the backend hub 33 stationary.

Figure 11D:
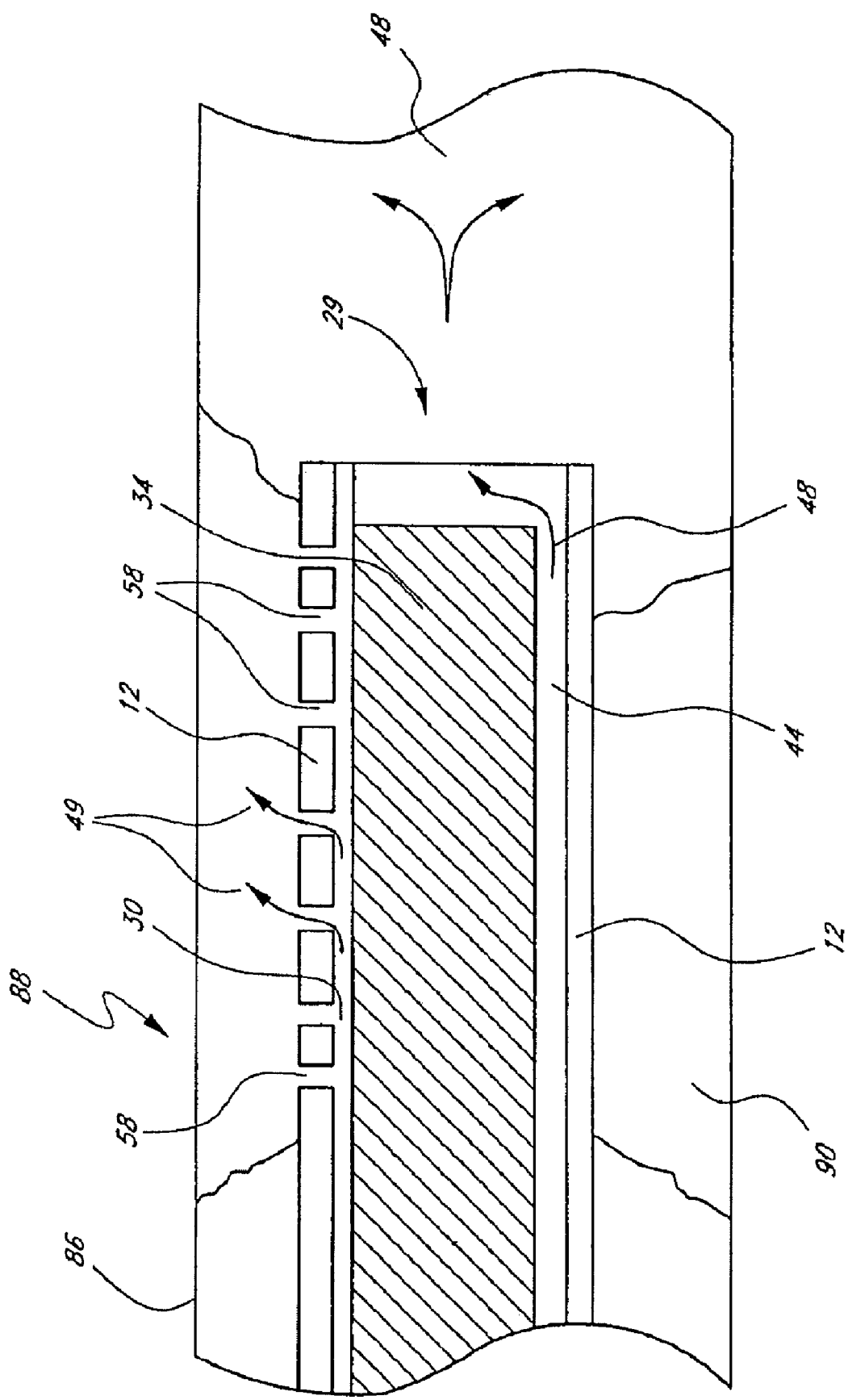
FIG. 11D is a cross-sectional view of the distal end of the ultrasonic catheter of FIG. 11C, wherein an inner core has been inserted into the tubular body to perform a treatment.

Still referring to FIG. 11D, arrows 48 indicate that a cooling fluid can be delivered through the cooling fluid lumen 44 and out the distal exit port 29. Likewise, arrows 49 indicate that a therapeutic compound can be delivered through the fluid delivery lumen 30 and out the fluid delivery ports 58 to the treatment site 88.

The cooling fluid can be delivered before, after, during or intermittently with the delivery of ultrasonic energy. Similarly, the therapeutic compound can be delivered before, after, during or intermittently with the delivery of ultrasonic energy. Consequently, the methods illustrated in FIGS. 11A through 11D can be performed in a variety of different orders than that described above. In an exemplary embodiment, the therapeutic compound and ultrasonic energy are delivered until the clot 90 is partially or entirely dissolved. Once the clot 90 has been sufficiently dissolved, the tubular body 12 and the inner core 34 are withdrawn from the treatment site 88.

Overview of a Small Vessel Ultrasonic Catheter.

Ultrasonic catheters can also be specifically configured to use in the small vessels of a patient's vasculature, such as in the vasculature of a patient's brain. In such a configuration, the catheter is provided with an energy delivery section having increased flexibility, thereby facilitating delivery of the catheter through narrow vessels having small radius turns. FIGS. 12A and 12B are cross-sectional views of the distal region of an exemplary ultrasonic catheter configured for use in the small vasculature.

Similar to the large vessel ultrasonic catheter described herein, an exemplary ultrasonic catheter configured for use in small vessels comprises a multi-component tubular body 202 having a proximal region and a distal region 206. In such embodiments, the catheter tubular body 202 includes an outer sheath 208 that is positioned upon an inner core 210. In one embodiment, the outer sheath 208 comprises extruded Pebax®, PTFE, polyetheretherketone ("PEEK"), PE, polyamides, braided polyamides and/or other similar materials. The outer sheath distal region 206 is adapted for advancement through vessels having a small diameter, such as those in the vasculature of the brain. In an exemplary embodiment, the outer sheath distal region 206 has an outer diameter between about 2 French and about 5 French. In another embodiment, outer sheath distal region 206 has an outer diameter of about 2.8 French. In one exemplary embodiment, the outer sheath 208 has an axial length of approximately 150 centimeters.

In a modified embodiment, the outer sheath 208 comprises a braided tubing formed of, for example, high or low density polyethylenes, urethanes, nylons, and the like. This configuration enhances the flexibility of the tubular body 202. For enhanced maneuverability, especially the ability to be pushed and rotated, the outer sheath 208 can be formed with a variable stiffness from the proximal to the distal end. To achieve this, a stiffening member may be included along the proximal end of the tubular body 202.

The inner core 210 defines, at least in part, a delivery lumen 212, which, in an exemplary embodiment, extends longitudinally along the catheter. The delivery lumen 212 has a distal exit port 214, and is hydraulically connected to a proximal access port (not shown). Similar to the large vessel ultrasonic catheter described herein, the proximal access port can be connected to a source of therapeutic compound or cooling fluid that is to be delivered through the delivery lumen 212.

In an exemplary embodiment, the delivery lumen 212 is configured to receive a guide wire (not shown). In such embodiments, the guidewire has a diameter of between approximately 0.008 and approximately 0.012 inches. In another embodiment, the guidewire has a diameter of about 0.010 inches. In an exemplary embodiment, the inner core 210 comprises polyamide or a similar material which can optionally be braided to increase the flexibility of the tubular body 202.

Still referring to FIGS. 12A and 12B, the tubular body distal region 206 includes an ultrasound radiating member 224. In such embodiments, the ultrasound radiating member 224 comprises an ultrasound transducer, which converts, for example, electrical energy into ultrasonic energy. In a modified embodiment, the ultrasonic energy can be generated by an ultrasound transducer that is remote from the ultrasound radiating member 224 and the ultrasonic energy can be transmitted via, for example, a wire to the ultrasound radiating member 224.

In the illustrated embodiment, the ultrasound radiating member 224 is configured as a hollow cylinder. As such, the inner core 210 extends through the lumen of the ultrasound radiating member 224. The ultrasound radiating member 224 is secured to the inner core 210 in a suitable manner, such as using an adhesive. A potting material can also be used to further secure the ultrasound radiating member 224 to the inner core 210.

In other embodiments, the ultrasound radiating member 224 can have a different shape. For example, the ultrasound radiating member 224 can take the form of a solid rod, a disk, a solid rectangle or a thin block. In still other embodiments, the ultrasound radiating member 224 can comprise a plurality of smaller ultrasound radiating members. The illustrated configuration advantageously provides enhanced cooling of the ultrasound radiating member 224. For example, in one embodiment, a therapeutic compound can be delivered through the delivery lumen 212. As the therapeutic compound passes through the lumen of the ultrasound radiating member 224, the therapeutic compound can advantageously remove excess heat generated by the ultrasound radiating member 224. In another embodiment, a fluid return path can be formed in the region 238 between the outer sheath 208 and the inner core 21 such that coolant from a coolant system can be directed through the region 238.

In an exemplary embodiment, the ultrasound radiating member 224 produces ultrasonic energy having a frequency of between about 20 kHz and about 20 MHz. In one embodiment, the frequency of the ultrasonic energy is between about 500 kHz and about 20 MHz, and in another embodiment the frequency of the ultrasonic energy is between about 1 MHz and about 3 MHz. In yet another embodiment, the ultrasonic energy has a frequency of about 3 MHz.

In the illustrated embodiment, ultrasonic energy is generated from electrical power supplied to the ultrasound radiating member 224 through a wires 226, 228 that extend through the catheter body 202. The wires 226, 228 cab be secured to the inner core 210, lay along the inner core 210 and/or extend freely in the region 238 between the inner core 210 and the outer sheath 208. In the illustrated configuration, the first wire 226 is connected to the hollow center of the ultrasound radiating member 224, while the second wire 228 is connected to the outer periphery of the ultrasound radiating member 224. In such embodiments, the ultrasound radiating member 224 comprises a transducer formed of a piezoelectric ceramic oscillator or a similar material.

Still referring to the exemplary embodiment illustrated in FIGS. 12A and 12B, the catheter further includes a sleeve 230 that is generally positioned about the ultrasound radiating member 224. The sleeve 230 is comprises a material that readily transmits ultrasonic energy. Suitable materials for the sleeve 230 include, but are not limited to, polyolefins, polyimides, polyester and other materials having a relatively low absorbance of ultrasonic energy. The proximal end of the sleeve 230 can be attached to the outer sheath 208 with an adhesive 232. To improve the bonding of the adhesive 232 to the outer sheath 208, a shoulder 227 or notch can be formed in the outer sheath 208 for attachment of the adhesive 232 thereto. In an exemplary embodiment, the outer sheath 208 and the sleeve 230 have substantially the same outer diameter.

In a similar manner, the distal end of the sleeve 230 can be attached to a tip 234. As illustrated, the tip 234 is also attached to the distal end of the inner core 210. In an exemplary embodiment, the tip 234 is between about 0.5 mm and about 4.0 mm long. In another embodiment, the tip is about 2.0 mm long. In the illustrated exemplary embodiment, the tip 234 is rounded in shape to reduce trauma or damage to tissue along the inner wall of a blood vessel or other body structure during advancement of the catheter to a treatment site.

Referring now to the exemplary embodiment illustrated in FIG. 12B, the catheter includes at least one temperature sensor 236 in the tubular body distal region 206. The temperature sensor 236 can be positioned on or near the ultrasound radiating member 224. Suitable temperature sensors include but are not limited to, diodes, thermistors, thermocouples, RTDs and fiber optic temperature sensors that used thermalchromic liquid crystals. In an exemplary embodiment, the temperature sensor 236 is operatively connected to a control system via a control wire that extends through the tubular body 202. As described above for the large vessel ultrasonic catheter, the control box includes a feedback control system having the ability to monitor and control the power, voltage, current and phase supplied to the ultrasound radiating member 224. Thus, the temperature along the relevant region of the catheter can be monitored and controlled for optimal performance. Details of the control box can also be found in U.S. patent application Ser. No. 10/309,388, filed 3 Dec. 2002, the entire disclosure of which is hereby incorporated herein by reference.

The small vessel ultrasound catheters disclosed herein can be used to remove an occlusion from a small blood vessel. In an exemplary method of use, a guidewire is percutaneously inserted into the patient's vasculature at a suitable insertion site. The guidewire is advanced through the vasculature toward a treatment site where the vessel is wholly or partially occluded. The guidewire is then directed at least partially through the thrombus.

After advancing the guidewire to the treatment site, the catheter is then inserted into the vasculature through the insertion site, and advanced along the guidewire towards the treatment site using, for example, over-the-guidewire techniques. The catheter is advanced until the tubular body distal region 206 is positioned near or in the occlusion. The tubular body distal region 206 optionally includes one or more radiopaque markers to aid in positioning the catheter at the treatment site.

After placing the catheter at the treatment site, the guidewire can then be withdrawn from the delivery lumen 212. A source of therapeutic compound, such as a syringe with a Luer fitting, can then be attached to the proximal access port. This allows the therapeutic compound to be delivered through the delivery lumen 212 and the distal exit port 214 to the occlusion.

The ultrasound radiating member 224 can then be activated to generate ultrasonic energy. As described above, in an exemplary embodiment, the ultrasonic energy has a frequency between about 20 kHz and about 20 MHz. In one embodiment, the frequency of the ultrasonic energy is between about 500 kHz and about 20 MHz, and in another embodiment the frequency of the ultrasonic energy is between about 1 MHz and about 3 MHz. In yet another embodiment, the ultrasonic energy has a frequency of about 3 MHz. The therapeutic compound and ultrasound energy can be applied until the occlusion is partially or entirely dissolved. Once the occlusion has been sufficiently dissolved, the catheter can be withdrawn from the treatment site.

Further information on exemplary methods of use, as well as on modified small vessel catheter constructions, are available in U.S. patent application Ser. No. 10/309,417, filed 3 Dec. 2002, the entire disclosure of which is hereby incorporated herein by reference.

Treatment of Vascular Occlusions Using Ultrasonic Energy and Microbubbles.

In certain embodiments, the therapeutic compound delivered to the treatment site includes a plurality of microbubbles having, for example, a gas formed therein. A therapeutic compound containing microbubbles is referred to herein as a "microbubble therapeutic compound". In an exemplary embodiment, the microbubbles are formed by entrapping micro spheres of gas into the therapeutic compound. In one embodiment, this is accomplished by agitating the therapeutic compound while blowing a gas into the therapeutic compound. In another embodiment, this is accomplished by exposing the therapeutic compound to ultrasonic energy with a sonicator under a gaseous atmosphere while vibrating the therapeutic compound. Other techniques can be used in other embodiments. Exemplary gases that are usable to form the microbubbles include, but are not limited to, air, oxygen, carbon dioxide, and inert gases. In one exemplary embodiment, the therapeutic compound includes approximately $4 \times 10^7$ microbubbles per milliliter of liquid. In one exemplary embodiment, the therapeutic compound includes between approximately $4 \times 10^6$ and approximately $4 \times 10^8$ microbubbles per milliliter of liquid. In one exemplary embodiment the microbubbles have a diameter of between approximately 0.1 μm and approximately 100 μm. Other parameters can be used in other embodiments.

In an exemplary embodiment, the efficacy of the therapeutic compound is enhanced by the presence of the microbubbles contained therein. In one embodiment, the microbubbles act as a nucleus for cavitation, and thus allow cavitation to be induced at lower levels of ultrasonic energy. Therefore, a reduced amount of ultrasonic energy can be delivered to the treatment site without reducing the efficacy of the treatment. Reducing the amount of ultrasonic energy delivered to the treatment site reduces risks associated with overheating the treatment site, and, in certain embodiments, also reduces the time required to treat a vascular occlusion. In certain embodiments, cavitation also promotes more effective diffusion and penetration of the therapeutic compound into surrounding tissues, such as the vessel wall and/or the clot material. Furthermore, in some embodiments, the mechanical agitation caused motion of the microbubbles is effective in mechanically breaking up clot material.

In an exemplary embodiment, a therapeutic compound containing microbubbles is delivered using the various embodiments of the ultrasonic catheters disclosed herein. However, in certain embodiments, modifications to the catheter design, and/or to the method of use, are implemented to improve the efficacy of a microbubble-based vascular occlusion treatment. In particular, these modifications are intended to reduce the destruction of microbubbles within the ultrasonic catheter. For example, the microbubbles occasionally burst when exposed to ultrasonic energy, regardless of whether that exposure occurs inside or outside the fluid delivery lumens of the ultrasonic catheter. Therefore, these modifications are intended to reduce the exposure of the microbubble therapeutic compound to ultrasonic energy before the microbubble therapeutic compound is expelled from the catheter and is delivered to the treatment site.

In one embodiment, a microbubble therapeutic compound is infused intra-arterially or intravenously to the treatment site before the ultrasound radiating members are activated. Therefore, once the ultrasound radiating members begin to generate ultrasonic energy, the microbubble therapeutic compound is already at the treatment site. In such embodiments, the microbubble therapeutic compound is delivered using the same catheter that is used to the deliver the ultrasonic energy. In a modified embodiment, the microbubble therapeutic compound is delivered using a different catheter than that used to deliver the ultrasonic energy, and delivery of the microbubble therapeutic compound to the treatment site is optionally via the general vascular circulation.

In an embodiment that is particularly advantageous for use with an ultrasonic catheter having a cylindrical ultrasound radiating member, such as illustrated in FIGS. 12A and 12B, an insulating chamber is used to reduce the amount of ultrasonic energy that is delivered into the catheter fluid delivery lumen. Specifically, an insulating chamber is positioned between the ultrasound radiating member and the delivery lumen. In such embodiments, the insulating chamber is filled with a material that does not efficiently transmit ultrasonic energy, thereby reducing the amount of ultrasonic energy reaching the fluid delivery lumen. Exemplary materials that can be put into the insulating chamber include, but are not limited to, air, nitrogen and oxygen. In a modified embodiment, an evacuated chamber is used.

Figure 13:
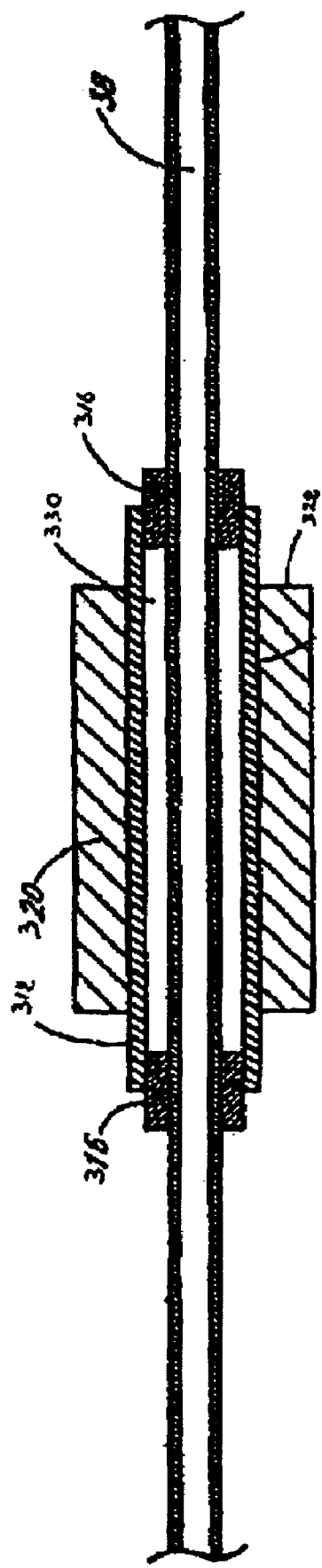
FIG. 13 is a cross-sectional view of an ultrasound radiating member separated from a delivery lumen by a chamber.

FIG. 13 illustrates an exemplary embodiment of an ultrasound catheter having an ultrasound radiating member 320 separated from a delivery lumen 338 by an insulating chamber 330. The ultrasound radiating member 320 is offset from the delivery lumen 338 using spacers 316 and support members 318. Other configurations can be used in other embodiments. Additional information on using chambers to spatially direct ultrasonic energy can be found in U.S. Pat. Nos. 6,582,392 and 6,676,626, the entire disclosure of which is incorporated herein by reference.

In a modified embodiment, the microbubble therapeutic compound is delivered from an ultrasonic catheter intermittently with ultrasonic energy. For example, in one such embodiment, during a first treatment phase, the microbubble therapeutic compound is delivered without ultrasonic energy.

Then, during a second treatment phase, delivery of the microbubble therapeutic compound is paused and ultrasonic energy is delivered to the treatment site. Optionally, the first and second treatment phases are alternately repeated several times. In one embodiment, the duration of the first and second phases are each on the order of approximately a few minutes. This configuration reduces the amount of cavitation occurring within the fluid delivery lumen of the ultrasonic catheter. In other embodiments, the therapeutic compound delivered to the treatment site is alternated between a therapeutic compound that contains microbubbles and a therapeutic compound that does not contain microbubbles. In such embodiments, the phases with ultrasonic energy correspond to the periods during which the therapeutic compound that does not contain microbubbles is applied.

Figure 14:
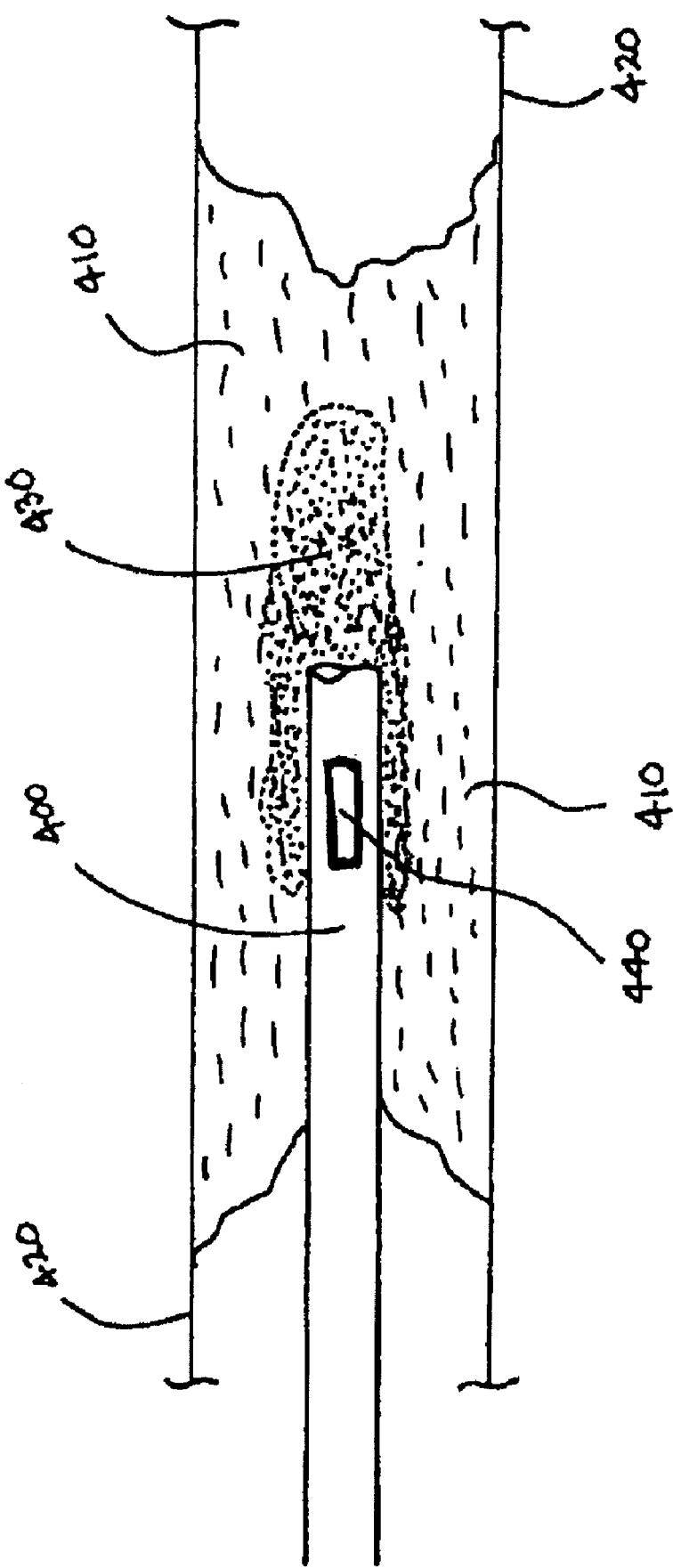
FIG. 14 is a cross-sectional view of an exemplary technique for applying ultrasonic energy to an infused microbubble therapeutic compound.

In one embodiment, the microbubble therapeutic compound is injected directly into a vascular obstruction—such as a clot—at the treatment site. A schematic illustration of this embodiment is provided in FIG. 14. Specifically, FIG. 14 illustrates a catheter 400 positioned within an occlusion 410 at a treatment site within a patient's vasculature 420. A microbubble therapeutic compound 430 has been infused into the occlusion 410 from the catheter 400. Once the microbubble therapeutic compound has been sufficiently infused, one or more ultrasonic radiating members 440 mounted within the catheter 400 can be energized, thereby delivering ultrasonic energy to the infused microbubble therapeutic compound 430. The catheter 400 is optionally repositioned to direct additional ultrasonic energy into the infused microbubble therapeutic compound 430. This technique allows microbubbles to be suspended within the obstruction. In such embodiments, ultrasonic energy is applied to the obstruction, thereby causing mechanical agitation of the microbubbles. The mechanical agitation of the microbubbles is effective in mechanically breaking up clot material.

SCOPE OF THE INVENTION

While the foregoing detailed description discloses several embodiments of the present invention, it should be understood that this disclosure is illustrative only and is not limiting of the present invention. It should be appreciated that the specific configurations and operations disclosed can differ from those described above, and that the methods described herein can be used in contexts other than treatment of vascular occlusions.

We claim:

1. A method of treating a vascular occlusion located at a treatment site within a patient's vasculature, the method comprising:
   positioning an ultrasound catheter at the treatment site;
   delivering a microbubble therapeutic compound from the ultrasound catheter to the vascular occlusion during a first treatment phase; and
   pausing the delivery of the microbubble therapeutic compound and delivering ultrasonic energy from the ultrasound catheter to the vascular occlusion during a second treatment phase while the delivery of microbubble therapeutic compound remains paused.

2. The method of claim 1, further comprising measuring a temperature at the treatment site during the second treatment phase, wherein a duration of the second treatment phase is at least partially dependent on the measured temperature.

3. The method of claim 1, wherein the first treatment phase has a duration between approximately one minute and approximately three minutes.

4. The method of claim 1, wherein the first treatment phase and the second treatment phase are approximately the same duration.

5. The method of claim 1, wherein the first treatment phase is longer than the second treatment phase.

6. The method of claim 1, wherein the first treatment phase is shorter than the second treatment phase.

7. The method of claim 1, further comprising repositioning the catheter after the first treatment phase and before the second treatment phase.

8. The method of claim 1, wherein the first and second treatment phases are alternately repeated a plurality of times.

9. The method of claim 1, wherein the microbubble therapeutic compound is infused from a catheter fluid delivery port positioned within the occlusion.

10. The method of claim 1, wherein the microbubble therapeutic compound is infused from a catheter fluid delivery port positioned external to the occlusion.

11. The method of claim 1, wherein the microbubble therapeutic compound includes between approximately $4 \times 10^6$ and approximately $4 \times 10^8$ microbubbles per milliliter.

12. The method of claim 1, wherein the microbubble therapeutic compound includes microbubbles having a diameter of between approximately 0.1 μm and approximately 100 μm.

13. A method of treating a vascular occlusion located at a treatment site within a patient's vasculature, the method comprising:
   passing an ultrasound catheter through the patient's vasculature to the treatment site, wherein the ultrasound catheter includes at least one fluid delivery port;
   positioning the ultrasound catheter at the treatment site such that the at least one fluid delivery port is positioned within the occlusion;
   infusing a microbubble therapeutic compound from the ultrasound catheter into an internal portion of the occlusion;
   pausing delivery of the microbubble therapeutic compound from the ultrasound catheter after a first quantity has been infused into the occlusion;
   delivering ultrasonic energy from the ultrasound catheter into the infused microbubble therapeutic compound;
   repositioning the ultrasound catheter at the treatment site; and
   infusing a second quantity of microbubble therapeutic compound from the ultrasound catheter to the treatment site after the ultrasonic energy is delivered to the treatment site.

14. The method of claim 13, wherein the ultrasonic energy is delivered for between about one minute and about three minutes.

15. The method of claim 13, wherein the microbubble therapeutic compound is delivered to the treatment site for a period of time that is approximately equal to a period of time during which ultrasonic energy is delivered to the treatment site.

16. The method of claim 13, further comprising measuring a temperature at the treatment site, wherein the quantity of ultrasonic energy delivered into the infused microbubble therapeutic compound is at least partially dependent on the measured temperature.

17. The method of claim 13, wherein the microbubble therapeutic compound includes between approximately $4 \times 10^6$ and approximately $4 \times 10^8$ microbubbles per milliliter.

18. The method of claim 13, wherein the microbubble therapeutic compound includes microbubbles having a diameter of between approximately 0.1 μm and approximately 100 μm21.

19. The method of claim 13, wherein the ultrasound catheter includes a plurality of ultrasound radiating members.

20. The method of claim 13, wherein the ultrasound radiating member comprises an ultrasound radiating member having a hollow inner core, and wherein the microbubble therapeutic compound is passed through the hollow inner core before being infused at the treatment site.

21. An ultrasound catheter system comprising:
- an elongate tubular body having an ultrasound radiating member and a fluid delivery lumen positioned therein;
- a fluid reservoir that is hydraulically coupled to a proximal portion of the fluid delivery lumen, the fluid delivery reservoir containing a microbubble therapeutic compound;
- an infusion pump configured to pump the microbubble therapeutic compound from the fluid reservoir into the fluid delivery lumen; and
- control circuitry configured to send electrical activation power to the infusion pump and to the ultrasound radiating member, wherein the control circuitry is configured such that the infusion pump and the ultrasound radiating member are not activated simultaneously.

22. The ultrasound catheter system of claim 21, further comprising a temperature sensor, wherein the control circuitry sends electrical activation power to one of the infusion pump and the ultrasound radiating member based on a temperature signal received from the temperature sensor.

23. The ultrasound catheter system of claim 21, wherein a plurality of ultrasound radiating members are positioned within the elongate tubular body.

24. The ultrasound catheter system of claim 21, wherein a plurality of fluid delivery lumens are positioned within the elongate tubular body.

25. The ultrasound catheter system of claim 21, wherein the tubular body has an outer diameter between about 2 French and about 5 French.

* * * * *

UNITED STATES PATENT AND TRADEMARK OFFICE
CERTIFICATE OF CORRECTION

PATENT NO.        : 7,648,478 B2                                    Page 1 of 1
APPLICATION NO.   : 12/046375
DATED             : January 19, 2010
INVENTOR(S)       : Soltani et al.

It is certified that error appears in the above-identified patent and that said Letters Patent is hereby corrected as shown below:

Title Page;

In item (56), page 2, column 2, line 46, under Other Publications, change "Wity" to --With--.

In item (56), page 2, column 2, line 51, under Other Publications, after "Circulation" insert --,--.

In item (56), page 2, column 2, line 58, under Other Publications, change "Liposheres" to --Lipospheres--.

At column 16, line 7, after "through" delete "a".

At column 16, line 8, change "cab" to --can--.

At column 20, line 67, in Claim 18, change "µm21." to --µm.--.

Signed and Sealed this
Twenty-ninth Day of March, 2011

David J. Kappos
*Director of the United States Patent and Trademark Office*